(12) United States Patent
Hayashi

(10) Patent No.: US 11,683,622 B2
(45) Date of Patent: Jun. 20, 2023

(54) HEADPHONE COVER AND FASTENER THEREFOR

(71) Applicant: Fifty Square Inc., Tokyo (JP)

(72) Inventor: Masayuki Hayashi, Tokyo (JP)

(73) Assignee: FIFTY SQUARE INC., Tokyo (JP)

( * ) Notice: Subject to any disclaimer, the term of this patent is extended or adjusted under 35 U.S.C. 154(b) by 103 days.

(21) Appl. No.: 17/600,338

(22) PCT Filed: Apr. 4, 2019

(86) PCT No.: PCT/JP2019/014984
§ 371 (c)(1),
(2) Date: Sep. 30, 2021

(87) PCT Pub. No.: WO2020/202535
PCT Pub. Date: Oct. 8, 2020

(65) Prior Publication Data
US 2022/0167070 A1    May 26, 2022

(51) Int. Cl.
*H04R 25/00* (2006.01)
*H04R 1/02* (2006.01)
*H04R 1/10* (2006.01)

(52) U.S. Cl.
CPC ........... *H04R 1/023* (2013.01); *H04R 1/1008* (2013.01); *H04R 1/1058* (2013.01)

(58) Field of Classification Search
CPC .... H04R 1/1008; H04R 1/105; H04R 1/1058; H04R 1/023; H04R 2205/022; H04R 5/0335; H04R 2201/10
See application file for complete search history.

(56) References Cited

U.S. PATENT DOCUMENTS 10,075,786 B2 * 9/2018 Larsen .................. H04R 1/023

FOREIGN PATENT DOCUMENTS

| JP | H06-44290 U | 6/1994 |
| JP | 2013-063217 A | 4/2013 |
| JP | 2015-133609 A | 7/2015 |

* cited by examiner

*Primary Examiner* — Amir H Etesam
(74) *Attorney, Agent, or Firm* — Polsinelli PC

(57) ABSTRACT

The present invention is provided with a fabric (11) for covering an ear pad (101) and a ring-shaped member (15) that is formed separately from the fabric (11) and acts in a direction towards the inner peripheral surface of the ear pad (101) from a recessed space (105) formed between the ear pad (101) in order to fix a portion of the fabric (11) to the inner peripheral surface of the ear pad (101) or its vicinity. The ear pad (101) is covered with the fabric (11) in a state in which the opening peripheral edge portion of the fabric (11) is fixed by elastic webbing (13) to the outer peripheral surface of the ear pad (101) or a housing (102), while a portion of the fabric (11) is fixed to a bottom portion of the inner peripheral surface of the ear pad (101) by the ring-shaped member (15). As a result, the recessed space (105) in the middle of the ear pad (101) is not closed by the fabric (11) even in a state in which the ear pad (101) is covered by the fabric (11), and a headphone (100) can be used with a sense of use similar to that of an around ear type.

12 Claims, 14 Drawing Sheets

(a)        (b)

(a)

(b)

(a)

(b)

HEADPHONE COVER AND FASTENER THEREFOR

CROSS REFERENCE TO RELATED APPLICATIONS

This application is a National Phase filing under 35 U.S.C. § 371 of PCT/JP2019/014984 filed on Apr. 4, 2019, the entire contents of which are hereby incorporated by reference.

TECHNICAL FIELD

The present invention relates to a headphone cover and its fastener, and more particularly, to a headphone cover used covering an ear pad (earmuff) of an around ear type headphone and a fastener for fastening the headphone cover to the ear pad.

BACKGROUND ART

Conventionally, a headphone cover used covering an ear pad of a headphone is known (see, for example, Patent Literature 1). The headphone cover disclosed in Patent Literature 1 is a headphone cover formed by folding back a peripheral edge portion of a stretchable fabric to one surface side over the entire circumference of the peripheral edge portion and forming an opening in the one surface side and configured such that an elastic webbing is sewn to the fabric of an opening peripheral edge portion corresponding to the peripheral edge of the opening.

Attaching the headphone cover configured as described above to an ear pad makes it possible to eliminate discomfort caused by stickiness and stuffiness of the sweat and fat of the user using the headphone. That is, attaching the headphone cover made of a hygroscopic cloth to an ear pad makes it possible to reduce the stuffiness of the ear and prevent the discomfort caused by the stuffiness from occurring even when the user listens to music with the headphone for a long time.

Note that when a headphone cover is attached to an ear pad of an around ear type headphone (a type having a recessed space in the middle portion of an ear pad in which the ear is inserted and fitted (also called the over ear type)), the recessed space formed by the ear pad is blocked by the headphone cover, so that the sense of use is similar to that of an on-ear type headphone to which the ear is fixed by being pressed.

Patent Literature 1: JP 2015-133609 A

SUMMARY OF INVENTION

Technical Problem

There are advantages and disadvantages of the around ear type headphone and the on-ear type headphone. Since the around ear type covers the entire ear, surrounding noise can be shut out to some extent and the ear comes close to the side of the loudspeaker, there is an advantage of allowing the user to hear a more powerful sound. On the other hand, the on-ear type can be configured to be compact and lightweight and has an advantage that it is difficult for the user to feel the weight even if the user wears the headphones.

Accordingly, there is a need for a user who uses the around ear type headphones to enjoy music with a sense of use similar to that of the around ear type even when the user attaches the headphone cover to the ear pad.

The present invention has been made to meet such needs and has as its object to enable the user to use an around ear type headphone attached with a headphone cover with a sense of use similar to that of an around ear type.

Solution to Problem

In order to solve the above problems, a headphone cover according to the present invention includes a fabric for covering an ear pad from its outer peripheral surface to its inner peripheral surface and a fixing member for fixing a part of the fabric on the inner peripheral surface of the ear pad or its vicinity. An opening peripheral edge portion corresponding to a peripheral edge of an opening formed at a predetermined position of the fabric is configured to be fixable to the outer peripheral surface of the ear pad or the outer peripheral surface of a housing. In addition, a fixing member formed separately from the fabric is configured to act in a direction from a recessed space formed inside the ear pad toward the inner peripheral surface of the ear pad to be able to fix a part of the fabric to the inner peripheral surface of the ear pad or its vicinity.

Advantageous Effects of Invention

According to the present invention configured as described above, the ear pad is covered with the fabric from the outer peripheral surface to the inner peripheral surface of the ear pad in a state in which the opening peripheral edge portion of the fabric is fixed to the outer peripheral surface of the ear pad or the outer peripheral surface of the housing, and a part of the fabric is fixed to the inner peripheral surface of the ear pad or its vicinity with the fixing member. Accordingly, even when the ear pad is covered with the fabric of the headphone cover, the recessed space formed in the middle portion of the ear pad can be prevented from being blocked by the fabric of the headphone cover. This enables the user to use an around ear type headphone attached with a headphone cover according to the present invention with a sense of use similar to that of an around ear type.

DESCRIPTION OF EMBODIMENTS

First Embodiment

Figure 1:
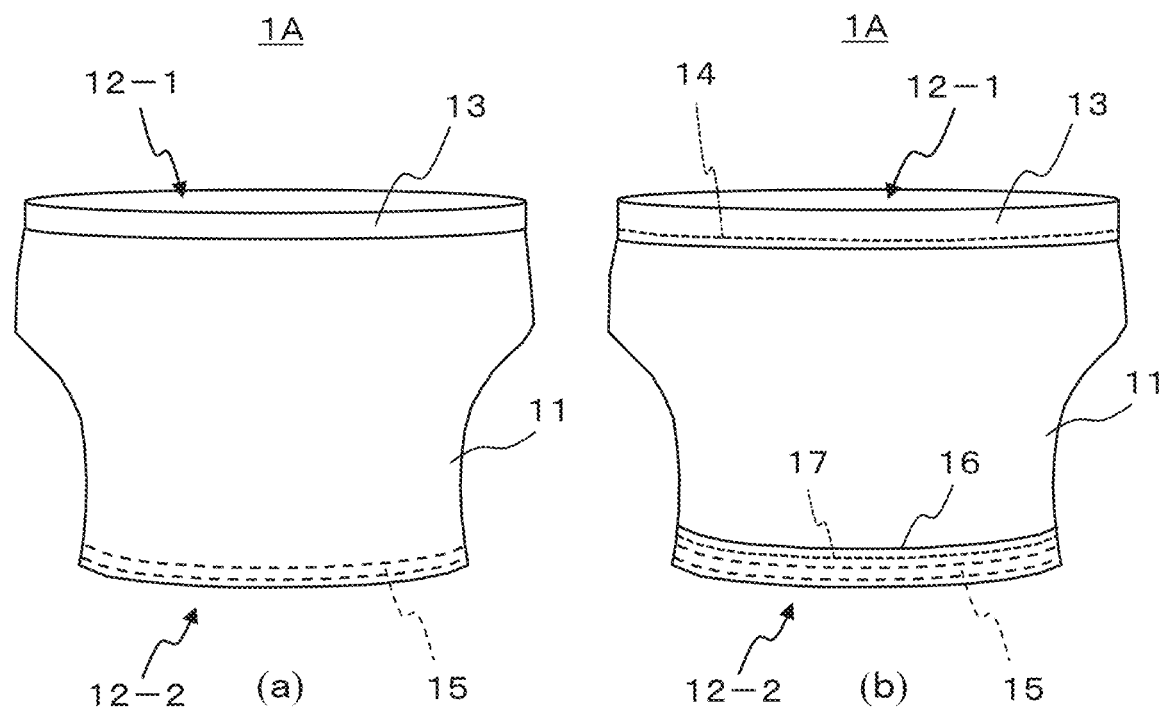
FIG. 1 is a diagram illustrating a configuration example of a headphone cover according to the first embodiment.
Figure 1:
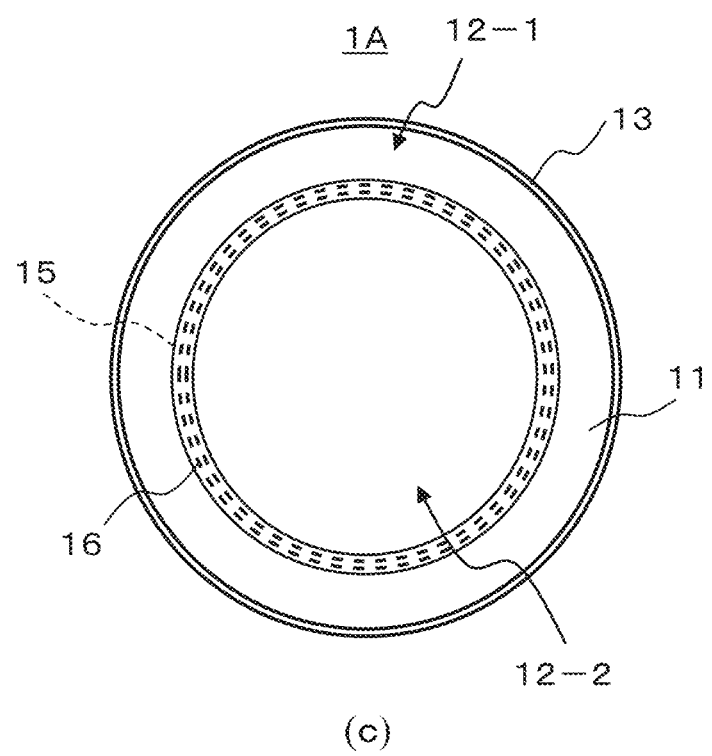

A headphone cover according to the first embodiment of the present invention will be described with reference to the accompanying drawings. FIG. 1 is a diagram illustrating a configuration example of a headphone cover 1A according to the first embodiment, with (a) illustrating the obverse of an obverse surface, (b) illustrating the reverse of the obverse surface, and (c) illustrating an upper surface. The headphone cover 1A according to the present embodiment has elasticity and is deformable. FIG. 1 illustrates one aspect of the shape of the headphone cover 1A in a steady state in which no external force is applied.

As will be described later with reference to FIG. 2, the headphone cover 1A according to the present embodiment is used which being fitted on an ear pad 101 of an around ear type headphones 100. Since the ear pad 101 is formed in a ring shape, a central portion of the around ear type headphone 100 is recessed, and a cylindrical recessed space 105 is formed in the space.

As illustrated in FIG. 1, the headphone cover 1A according to the present embodiment includes a fabric 11 for covering the ear pad 101 from its outer peripheral surface to its inner peripheral surface when the headphone cover 1A is attached to the headphone 100. Openings 12-1 and 12-2 are formed at predetermined positions on the fabric 11.

In the first embodiment, the fabric 11 is formed in a tubular shape, and the first opening 12-1 is formed in one end of the tubular shape while the second opening 12-2 is formed in the other end of the tubular shape. Both of the two openings 12-1 and 12-2 are formed in a circular shape, and the second opening 12-2 is formed to have a smaller diameter than the first opening 12-1.

In this case, the diameter of the first opening 12-1 is smaller than the diameter of a circle formed by the outer peripheral surface of the ear pad 101 or the outer peripheral surface of a housing 102 (in particular, a portion in contact with the ear pad 101) of the headphone 100 to be attached to the headphone cover 1A. In order to simplify the description below, as illustrated in FIG. 2, the headphone 100 to which the headphone cover 1A is attached is configured such that the outer peripheral surface of the ear pad 101 is flush with the outer peripheral surface of the portion of the housing 102 which is in contact with the ear pad 101 so as to be continuous with each other, and the diameter of the circle formed by the outer peripheral surface of the ear pad 101 is the same as the diameter of the circle formed by the outer peripheral surface of the portion of the housing 102 which is in contact with the ear pad 101.

Assume the outer peripheral surface of the ear pad 101 and the outer peripheral surface of the portion of the housing 102 which in contact with the ear pad 101 are discontinuous, and the diameter of the circle formed by the outer peripheral surface of the portion of the housing 102 which is in contact with the ear pad 101 is smaller than the diameter of the circle formed by the outer peripheral surface of the ear pad 101. In this case, the diameter of the first opening 12-1 is preferably smaller than the diameter of the outer peripheral surface of the housing 102. In this way, the headphone cover 1A can be attached to not only the headphone 100 of a type with the outer peripheral surface of the ear pad 101 being continuous with the outer peripheral surface of the housing 102 but also a headphone (not illustrated) of a type with the outer peripheral surface of the ear pad not being continuous with the outer peripheral surface of the housing while the headphone cover 1A is fitted to the headphone.

Furthermore, the diameter of the second opening 12-2 is substantially equal to the diameter of the circle formed by the inner peripheral surface of the ear pad 101. However, since the fabric 11 around the second opening 12-2 is stretchable, the diameter of the second opening 12-2 may be slightly smaller or larger than the diameter of the circle formed by the inner peripheral surface of the ear pad 101. When the fabric 11 having high stretchability is used, the diameter of the second opening 12-2 may be set to be about the same as or slightly smaller than or larger than the diameter of the circle formed by the inner peripheral surface of the ear pad 101, and the diameter of the first opening 12-1 may be set to be about the same as the diameter of the circle.

As described above, it is preferable to design the diameters of the two openings 12-1 and 12-2 so as to satisfy the relationship of (diameter of circle formed by inner peripheral surface of ear pad 101)≈(diameter of second opening 12-2)<(diameter of first opening 12-1)<(diameter of circle formed by the outer peripheral surface of ear pad 101 (or housing 102)).

An elastic body 13 is provided at a first opening peripheral edge portion corresponding to the peripheral edge of the first opening 12-1. The elastic body 13 is for fixing the first opening peripheral edge portion of the fabric 11 to the outer peripheral surface of the ear pad 101 or the outer peripheral surface of the housing 102 when the headphone cover 1A is attached to the headphones 100. That is, since the elastic body 13 is provided along the opening peripheral edge portion of the first opening 12-1 formed so as to satisfy the relationship of (diameter of first opening 12-1)<(diameter of circle formed by outer peripheral surface of ear pad 101 (or housing 102)), the first opening peripheral edge portion of the fabric 11 is fixed to the outer peripheral surface of the ear pad 101 or the outer peripheral surface of the housing 102 with a force that causes the elastic body 13 to contract to the original state by extending the elastic body 13 and hooking it on the outer peripheral surface of the ear pad 101 or the outer peripheral surface of the housing 102.

In the present embodiment, elastic webbing is used as an example of the elastic body 13 (to be referred to as the elastic webbing 13 hereinafter). More specifically, the elastic webbing 13 is sewn to the fabric 11 of the first opening peripheral edge portion of the first opening 12-1 with a thread 14. The thread 14 used here preferably has stretchability. The elastic webbing 13 is used because it can be sewn to the fabric 11 easily as compared with round rubber.

In this case, size setting is performed such that the length of the circumference of the elastic webbing 13 in the non-stretched state is substantially the same as the length of the circumference of the end portion of the fabric 11 in the non-stretched state. The length of the sewing thread 14 is set to be longer than the length of the entire circumference of the elastic webbing 13 in the most contracted state (the length of the circumference of the elastic webbing 13 in the steady state illustrated in FIG. 1). Then, a thread is sewn substantially parallel to the longitudinal direction (circumferential direction) of the elastic webbing 13. More specifically, the end of the fabric 11 and the elastic webbing 13 are stitched together in a state in which the fabric 11 and the elastic webbing 13 are stretched together.

In this manner, the headphone cover 1A according to the present embodiment is configured such that the length of the thread 14 used for sewing is made longer than the entire circumference of the elastic webbing 13 in the steady state. Accordingly, when the elastic webbing 13 is most contracted (not stretched), the thread 14 is slackened. In this state, the elastic webbing 13 can be stretched beyond the limit of the stretch of the thread 14 itself by the amount of the stretch margin from the state in which the thread 14 is slackened to the state in which the thread 14 is not slackened. This makes it possible to use one type of headphone cover 1A for headphones 100 having as many sizes as possible. Furthermore, one type of the headphone cover 1A can be used for not only the headphone 100 having the ear pad 101 and the housing 102 whose cross-sectional shapes are circular but also the headphones 100 having various shapes.

At the second opening peripheral edge portion corresponding to the peripheral edge of the second opening 12-2, a ring-shaped member 15 (an example of a fixing member and a fastener in the claims) for fixing a part of the fabric 11 to the inner peripheral surface of the ear pad 101 or its vicinity when the headphone cover 1A is attached to the headphone 100 is provided. In the present embodiment, the part of the fabric 11 is the second opening peripheral edge portion of the second opening 12-2. That is, the ring-shaped member 15 is configured separately from the fabric 11 and acts in a direction from the recessed space 105 formed inside the ear pad 101 toward the inner peripheral surface of the ear pad 101 (this point is the same in other embodiments described later) to fix the second opening peripheral edge portion of the fabric 11 to the inner peripheral surface of the ear pad 101 or its vicinity. The cross-sectional shape of the ring-shaped member 15 is arbitrary. For example, the ring-shaped member 15 may have a ring shape having a flat plate shape (rectangular cross section) or a ring shape having a cylindrical shape (circular cross section).

The ring-shaped member 15 is made of a material that can be deformed between a state of narrowing inward and a state of spreading outward and is configured to spread outward to be able to maintain a state of being deformed until a part (second opening peripheral edge portion) of the fabric 11 is guided to the inner peripheral surface of the ear pad 101 or its vicinity. As an example, the ring-shaped member 15 is a flexible resin member, can be deformed into a state of narrowing inward by applying an external force, and has a restoring force to spread outward to return to the original ring shape when the application of the external force is stopped.

That is, in the process in which the ring-shaped member 15 deformed to the state of narrowing inward by applying an external force spreads outward and returns to the original ring shape by stopping the application of the external force, the ring-shaped member 15 guides the second opening peripheral edge portion of the fabric 11 to the inner peripheral surface of the ear pad 101 or its vicinity. The ring-shaped member 15 then acts to maintain a state in which the second opening peripheral edge portion of the fabric 11 abuts on the inner peripheral surface of the ear pad 101 or the reverse surface of the ear pad 101 near the inner peripheral surface of the ear pad 101 or a state in which the ring-shaped member 15 returns to the original ring shape (a state in which the second opening peripheral edge portion of the fabric 11 is located near the inner peripheral surface of the ear pad 101).

Note that the ring-shaped member 15 may be a shape memory alloy wire (memory wire) made of a metal material such as copper, brass, aluminum, stainless steel, or iron.

The ring-shaped member 15 is embedded in a bag-shaped portion 16 formed in a part (the second opening peripheral edge portion of the second opening 12-2 in the present embodiment) of the fabric 11 (referring to FIG. 1(c), the bag-shaped portion 16 is schematically deformed). Thus, the fabric 11 and the ring-shaped member 15 are integrally formed (the fabric 11 and the ring-shaped member 15 cannot be separated). As illustrated in FIG. 1(b), the bag-shaped portion 16 is formed by folding back the second opening peripheral edge portion of the fabric 11 from the front side to the back side over the entire circumference and sewing the side close to the distal end of the folded portion with a yarn 17.

More specifically, the ring-shaped member 15 is placed at a position close to the second opening peripheral edge portion of the fabric 11, and the ring-shaped member 15 is covered with the fabric 11 by folding the second opening peripheral edge portion of the fabric 11 from the front side to the back side over the entire circumference. In this state, the ring-shaped member 15 is embedded in the bag-shaped portion 16 by sewing the side close to the distal end of the folded portion with the yarn 17 over the entire circumference.

Instead of sewing the elastic webbing 13 to the first opening peripheral edge portion of the fabric 11, the first opening peripheral edge portion may also constitute a bag-shaped portion in the same manner as the bag-shaped portion 16, and a round rubber or an elastic webbing may be embedded in the bag-shaped portion. In addition, the fabric 11 may be made of a material having an elastic force so as not to provide an elastic body such as elastic webbing 13 at the first opening peripheral edge portion. In this case, the elastic force of the opening peripheral edge portion may be increased by folding back and sewing the first opening peripheral edge portion doubly or more.

Figure 2:
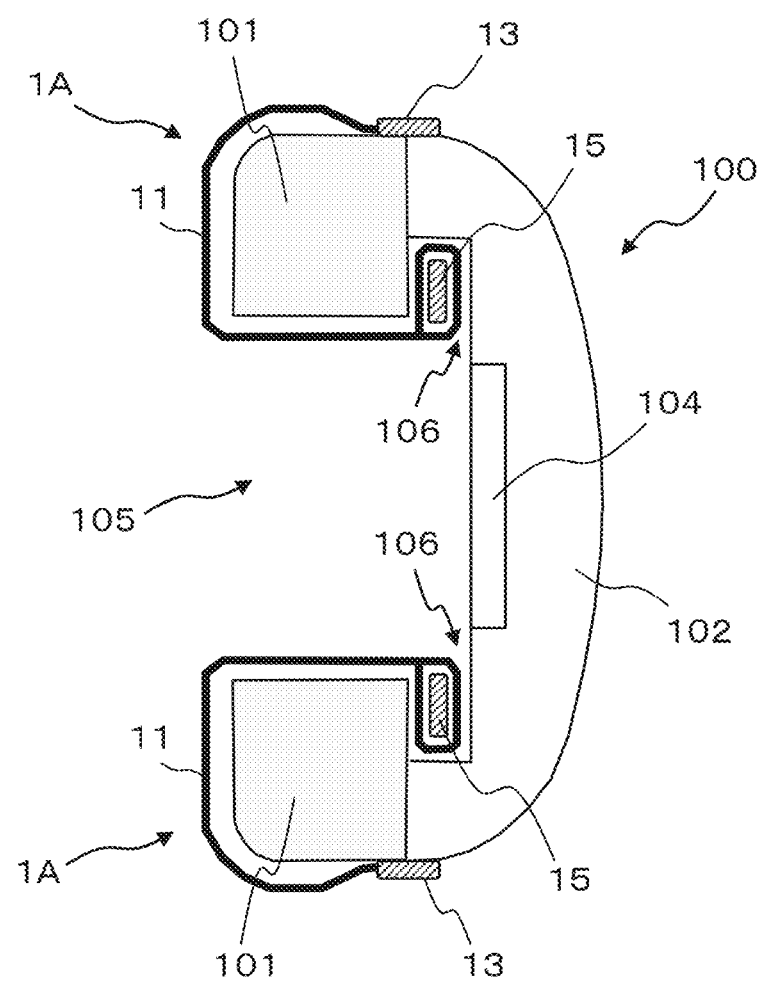
FIG. 2 is a schematic diagram illustrating a state in which the headphone covers according to the first embodiment are attached to the headphone.

FIG. 2 is a schematic diagram illustrating a state in which the headphone cover 1A configured as described above is attached to the headphones 100. FIG. 2 illustrates a cross section of one headphone unit of the headphone 100 including the headband and the pair of headphone units and the headphone cover 1A attached to the headphone unit as a simple schematic diagram.

As described above, in the case of the around ear type headphone 100, the middle portion of the ring-shaped ear pad 101 is recessed, and the cylindrical recessed space 105 is formed in the middle portion. The loudspeaker unit 104 exists at the bottom portion of the recessed space 105. In addition, a gap 106 is formed between the reverse surface of the ear pad 101 and the housing 102 exists at the bottom portion of the inner peripheral surface of the ear pad 101.

The ring-shaped member 15 is sized to fit in the gap 106 and fixes the second opening peripheral edge portion of the fabric 11 to near the inner peripheral surface of the ear pad 101 inside the gap 106. In this case, as long as the headphone 100 is formed to have a size such that the inner diameter of the gap 106 formed in the ring shape (=diameter of inner peripheral surface of ear pad 101) is smaller than the outer diameter of the ring-shaped member 15 in the most spread state (original ring-shaped state), even the headphones 100 having different sizes and shapes can fix the second opening peripheral edge portion of the fabric 11 near the inner peripheral surface of the ear pad 101 in a state in which the ring-shaped member 15 is placed in the gap 106.

Since the ear pad 101 is made of a cushion material having an elastic force, the ring-shaped member 15 can be inserted into the gap 106 even if the ring-shaped member 15 is actually formed to be slightly thicker than the gap 106. When the ring-shaped member 15 is configured to have such a size, it is possible to make the ring-shaped member 15 inserted into the gap 106 less likely to come off by receiving pressure or frictional force from the reverse surface of the ear pad 101.

Note that the ring-shaped member 15 is not necessarily sized to abut on the reverse surface of the ear pad 101 when inserted into the gap 106. That is, the ring-shaped member 15 may have such a size that a slight gap is formed between the ring-shaped member and the reverse surface of the ear pad 101. In this case, the ring-shaped member 15 acts to maintain a state in which the second opening peripheral edge portion of the fabric 11 abuts on the inner peripheral surface of the housing 102 corresponding to the deep position of the gap 106 or a state in which the ring-shaped member 15 returns to the original ring shape in the gap 106. As described above, even in a case in which the ring-shaped member 15 is configured to have such a size that a gap is formed between the ring-shaped member and the reverse surface of the ear pad 101, when the fabric 11 of the portion covering the inner peripheral surface or the outer peripheral surface of the ear pad 101 is pulled, the ring-shaped member (actually, the fabric 11 covering the ring-shaped member 15) abuts on the reverse surface of the ear pad 101 in the gap 106, so that the ring-shaped member 15 is less likely to come off from the gap 106.

When the headphone cover 1A is to be attached to the headphones 100, for example, the ring-shaped member 15 (the second opening peripheral edge portion of the fabric 11) is inserted into the gap 106 over the entire circumference while deforming the ring-shaped member 15 embedded in the bag-shaped portion 16 formed in the second opening peripheral edge portion of the fabric 11 in a state in which the reverse surface of the headphone cover 1A is on the outer side (a state in which the reverse surface is visible from the outside), as illustrated in FIG. 1(b).

Next, the inner peripheral surface and the outer peripheral surface of the ear pad 101 are sequentially covered with the fabric 11 while the fabric 11 is reversed such that the surface of the fabric 11 can be seen from the outside. And then, hooking the elastic webbing 13 sewn to the first opening peripheral edge portion of the fabric 11 on the outer peripheral surface of the ear pad 101 or the housing 102 fixes the first opening peripheral edge portion of the fabric 11 to the outer peripheral surface of the ear pad 101 or the housing 102.

Note that it is also possible to attach the headphone cover 1A in a reverse procedure. That is, hooking the elastic webbing 13 sewn to the first opening peripheral edge portion of the fabric 11 on the outer peripheral surface of the ear pad 101 or the housing 102 fixes the first opening peripheral edge portion of the fabric 11 to the outer peripheral surface of the ear pad 101 or the housing 102 in a state in which the surface of the headphone cover 1A is placed outside (seen from outside), as illustrated in FIG. 1(a).

Then, the outer peripheral surface and the inner peripheral surface of the ear pad 101 are sequentially covered with the fabric 11, and the ring-shaped member 15 (the second opening peripheral edge portion of the fabric 11) is inserted into the gap 106 over the entire circumference while the ring-shaped member 15 embedded in the bag-shaped portion 16 formed in the second opening peripheral edge portion of the fabric 11 is deformed.

As described above, the first opening peripheral edge portion of the fabric 11 is fixed to the outer peripheral surface of the ear pad 101 or the housing 102 by the elastic webbing 13, and the second opening peripheral edge portion of the fabric 11 is fixed to the vicinity of the inner peripheral surface of the ear pad 101 by the ring-shaped member 15 in the gap 106 formed in the bottom portion of the inner peripheral surface of the ear pad 101 (between the reverse surface of the ear pad 101 and the housing 102). In this state, the outer peripheral surface and the inner peripheral surface of the ear pad 101 are covered with the fabric 11. In FIG. 2, the fabric 11 is illustrated in a state of being separated from the ear pad 101 for easy understanding of appearance, but in practice, the fabric 11 can be fitted from the outer peripheral surface to the inner peripheral surface of the ear pad 101.

In this way, even when the ear pad 101 is covered with the fabric 11 of the headphone cover 1A, the cylindrical recessed space 105 formed in the middle portion of the ear pad 101 can be prevented from being blocked by the fabric 11 of the headphone cover 1A. This enables the user to use an around ear type headphone 100 attached with the headphone cover 1A according to the present embodiment with a sense of use similar to that of an around ear type.

Figure 3:
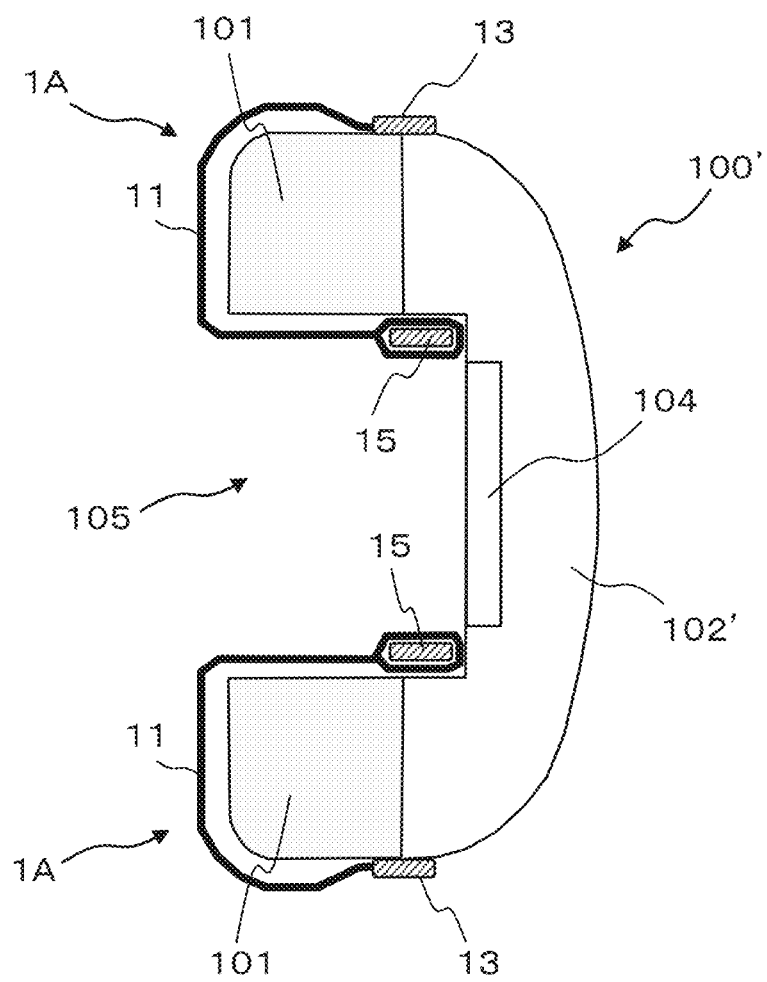
FIG. 3 is a diagram illustrating a state in which the headphone covers according to the first embodiment is attached to another type of headphone.

FIG. 3 is a diagram illustrating a state in which the headphone covers 1A according to the present embodiment are attached to another type of headphone 100'. FIG. 3 illustrates a state in which the headphone cover 1A is attached to the headphone 100' of a type having no gap at a bottom portion of the inner peripheral surface of the ear pad 101. In this case, the second opening peripheral edge portion of the fabric 11 is fixed to the bottom portion of the inner peripheral surface of the ear pad 101 or the inner peripheral surface of a housing 102' with the ring-shaped member 15, and the ear pad 101 is covered with the fabric 11.

In this case, as long as the headphone 100 is formed to have a size such that the diameter of the inner peripheral surface of the ear pad 101 is smaller than the outer diameter of the ring-shaped member 15 in the most spread state (original ring-shaped state), even the headphones 100 having different sizes and shapes can fix the second opening peripheral edge portion of the fabric 11 to the inner peripheral surface of the ear pad 101 in a state in which the ring-shaped member 15 is pressed against the inner peripheral surface of the ear pad 101.

On the other hand, assume that the headphone 100 is formed to have a size that makes the diameter of the inner peripheral surface of the ear pad 101 larger than the outer diameter of the ring-shaped member 15 in the most spread state (original ring-shaped state). Even in this case, when the difference between the diameters is not large, the second opening peripheral edge portion can be fixed to the vicinity of the inner peripheral surface of the ear pad 101 by guiding the second opening peripheral edge portion of the fabric 11 to the vicinity of the inner peripheral surface of the ear pad 101 by the ring-shaped member 15. In this case, a part of the fabric 11 is separated from the inner peripheral surface of the ear pad 101, but the sense of use similar to that of the around ear type is not impaired.

Figure 4:
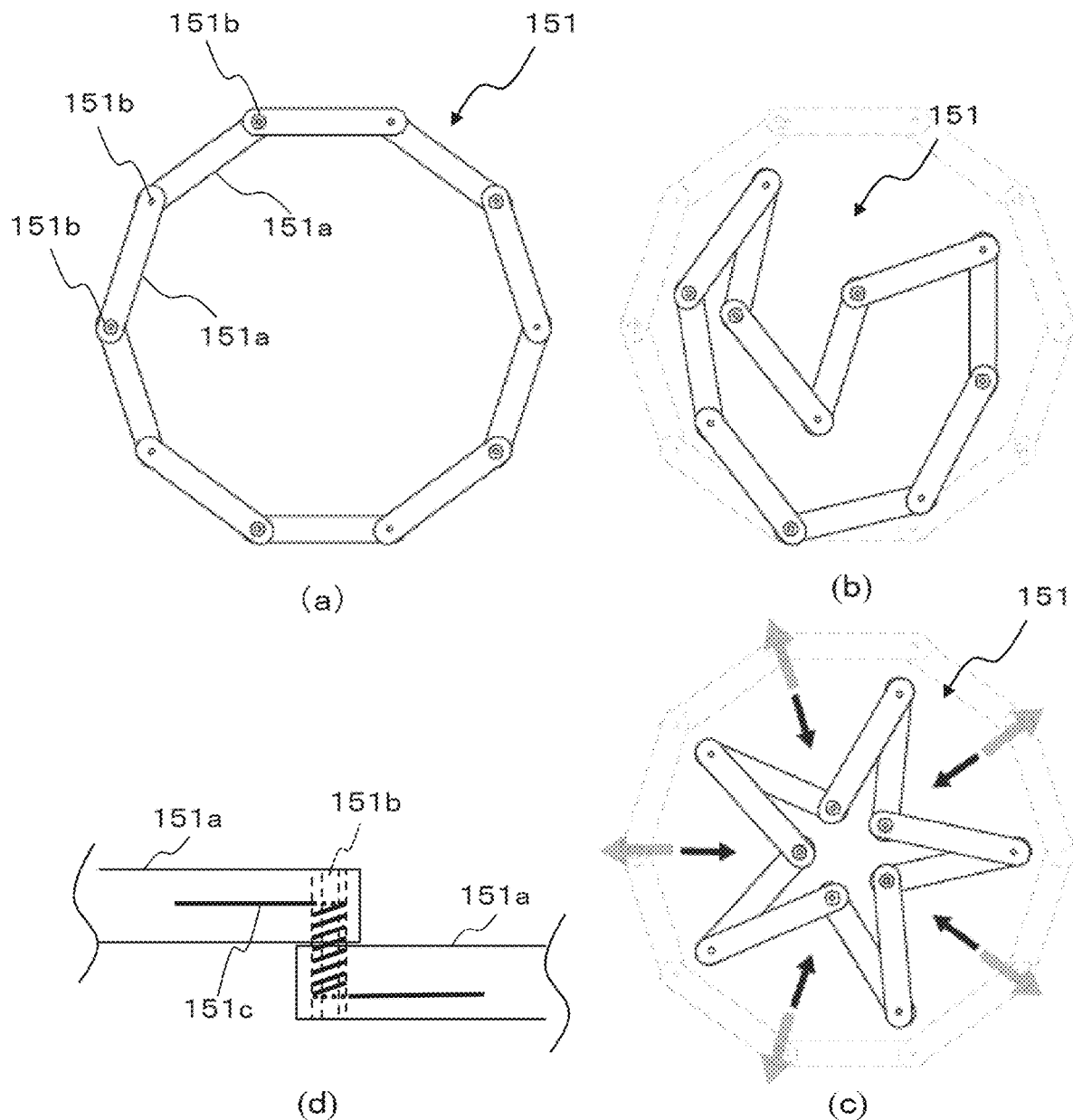
FIG. 4 is a view illustrating another example of a fixing member.

The above embodiment has exemplified the ring-shaped member 15 made of a resin having flexibility as a fixing member that can be deformed by the application of an external force and has the restoring force to return to the original ring shape upon stopping the application of the external force. However, the fixing member is not limited to this. For example, as illustrated in FIG. 4, the fixing member may be configured by a ring-shaped member 151 configured to have a ring shape as a whole by sequentially connecting a plurality of plates 151a. Each plate 151a may be made of any material such as metal or resin.

Each of the plurality of plates 151a is connected to another plate 151a through a rotation shaft 151b provided near both ends and is configured to be pivotal about the rotation shaft 151b. The example in FIG. 4 illustrates a configuration in which 10 rectangular plates 151a with chamfered corners are sequentially connected. In this case, by alternately connecting the plates 151a so as to be on the upper side and the lower side, a ring shape is formed by a space region having a thickness twice the thickness of one plate 151a.

FIG. 4(a) illustrates a state in which all the plates 151a are coupled at the same angle, and the ring-shaped member 151 forms a regular decagon (ring shape) as a whole. On the other hand, FIG. 4(b) illustrates a state in which the ring-shaped member 151 is deformed into an arbitrary shape by making the plurality of plates 151a pivot through an arbitrary angle. FIG. 4(c) illustrates a state in which the ring-shaped member 151 is deformed into a star shape as a whole by making the plurality of plates 151a pivot in such a manner that the portions of the five rotation shafts 151b are alternately pushed by the same amount in the central direction of the regular decagon.

The ring-shaped member 151 configured as illustrated in FIG. 4 is also embedded in the bag-shaped portion 16 formed in the second opening peripheral edge portion of the fabric 11 and is configured integrally with the fabric 11. When the headphone cover 1A is attached to the headphone 100 and the ring-shaped member 151 (the second opening peripheral edge portion of the fabric 11) is inserted into the gap 106, the ring-shaped member 151 is deformed as illustrated in FIG. 4(b) or 4(c). After the ring-shaped member 151 is inserted into the gap 106, the ring-shaped member 151 is brought into a state as illustrated in FIG. 4(a), and the ring-shaped member 151 is accommodated in the gap 106 over the entire circumference.

Note that the ring-shaped member 151 illustrated in FIG. 4 may have a restoring force to return from a deformed state (a state of narrowing inward) as illustrated in FIG. 4(b) or 4(c) to a ring shape (a state of spreading outward) as illustrated in FIG. 4(a) or may not have a restoring force. That is, the ring-shaped member 151 may be manually deformed from the folded state as illustrated in FIG. 4(b) or FIG. 4(c) to the state of being expanded into the ring shape as illustrated in FIG. 4(a) or may be automatically deformed by using a restoring force with which the ring-shaped member 151 tries to return to the original ring shape. As an example of a configuration for applying a restoring force to the ring-shaped member 151, a configuration using a torsion spring 151c as illustrated in FIG. 4(d) can be considered.

For example, a part or the whole of the inside of the plate 151a is hollow, and the torsion spring 151c is alternately wound around the rotation shafts 151b. Both legs of the torsion spring 151c are configured to abut on the inner walls of the two adjacent plates 151a one by one. With this configuration, when the user applies an external force to the ring-shaped member 151 to deform the ring-shaped member 151 into a star shape as illustrated in FIG. 4(c) and then stops applying the external force, the ring-shaped member 151 automatically returns to the ring shape as illustrated in FIG. 4(a) by receiving the restoring force of the torsion spring 151c wound around the five rotation shafts 151b near the center of the star shape.

Figure 5:
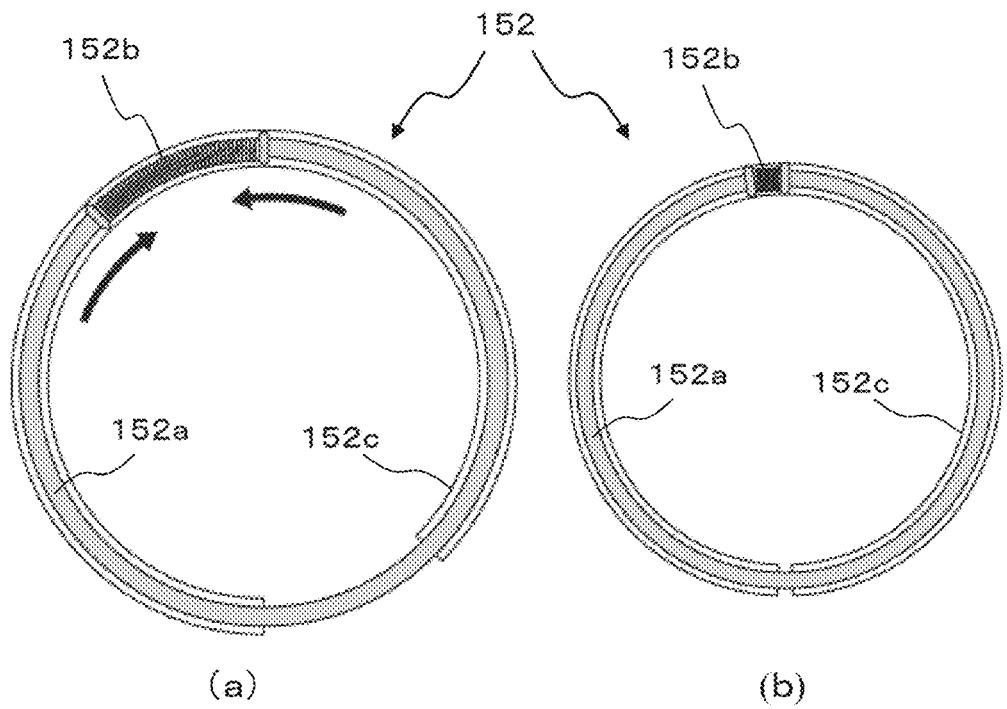
FIG. 5 is a view illustrating another example of the fixing member.

As another example of the fixing member that can be deformed by the application of an external force and has the restoring force to return to the original ring shape upon stopping the application of the external force, a ring-shaped member 152 configured as illustrated in FIG. 5 may be used. The ring-shaped member 152 illustrated in FIG. 5 includes, for example, a flexible member 152a made of resin and having flexibility and a spring member (For example, a coil spring 152b) disposed between both ends of the flexible member 152a and is configured to have a ring shape as a whole by the flexible member 152a and the coil spring 152b.

In the configuration in FIG. 5, the flexible member 152a and the coil spring 152b are configured as separately from each other. These members are inserted into the tube 152c to make the configuration have integrity as a whole. The tube 152c has a configuration with a part of the ring shape being lost to allow the coil spring 152b to be contracted without contracting or loosening the tube 152c. Note that both ends of the flexible member 152a and both ends of the coil spring 152b may be bonded to each other.

The ring-shaped member 152 configured as illustrated in FIG. 5 is also embedded in the bag-shaped portion 16 formed in the second opening peripheral edge portion of the fabric 11 and is configured integrally with the fabric 11. When the ring-shaped member 152 (the second opening peripheral edge portion of the fabric 11) is inserted into the gap 106 to attach the headphone cover 1A to the headphone 100, the user applies an external force to the ring-shaped member 152 to contract the coil spring 152b as illustrated in FIG. 5(b). After the ring-shaped member 152 is inserted into the gap 106, releasing the hand from the ring-shaped member 152 will cause the contracted coil spring 152b to extend to bring the ring-shaped member 152 into the state as illustrated in FIG. 5(a), thereby accommodating the ring-shaped member 152 in the gap 106 over the entire circumference.

The above embodiment has exemplified the case of using the ring-shaped members 15, 151, and 152, each having a predetermined diameter in the most spread state as a fixing member. However, the present invention is not limited to this. For example, as illustrated in FIG. 6(a), a belt-like member 15' formed in a ring shape may be used as a fixing member. The belt-like member 15' may be embedded in the bag-shaped portion 16 to be integrated with the fabric 11 or may be configured not to be integrated with the fabric 11 (in a state in which the fabric 11 and the belt-like member 15' can be separated).

When the fabric 11 and the belt-like member 15' are configured to be separable, for example, as illustrated in FIG. 6(b), a chipped portion 16a may be provided in a part of the bag-shaped portion 16, and the belt-like member 15' may be inserted (buried) into the bag-shaped portion 16 from the chipped portion 16a when the headphone cover 1A is used. In this case, both ends of the belt-like member 15' inserted into the bag-shaped portion 16 may be exposed from the chipped portion 16a, and the user may adjust the size of the diameter of the ring-shaped belt-like member 15' by sliding the both end portions of the belt-like member 15' by hand. This can extend the range in which the headphone cover 1A according to the present embodiment can be used for the headphones 100 having various sizes with the cylindrical recessed spaces 105 having different diameters.

When the belt-like member 15' as illustrated in FIG. 6(a) is used as a fixing member, a locking member that locks at least a part of the belt-like member 15' may be provided so as to stably maintain the ring-shaped state. FIG. 7 is a view illustrating an example of the locking member. Using such a locking member makes it possible to reliably maintain the adjusted diameter when the diameter of the ring shape is adjusted such that the belt-like member 15' is located on the inner peripheral surface of the ear pad 101 or its vicinity. This makes it possible to prevent the position of the belt-like member 15' from being easily displaced and allow the headphone cover 1A to keep stably covering the ear pad 101.

FIG. 7(a) illustrates a configuration example of a ring-shaped locking member 51 formed of, for example, a material such as an elastic vinyl chloride resin. The inner diameter of the ring-shaped locking member 51 is set to a value substantially equal to or slightly smaller than the thickness of two overlapping belt-like members 15'. The ring-shaped locking member 51 configured in this manner is brought into pressure contact with overlapping portions of the belt-like members 15' in a state in which the both ends of the belt-like members 15' are inserted through the ring-shaped locking member 51 in opposite directions. As a result, the belt-like member 15' inserted into the ring-shaped locking member 51 is tightened by the ring-shaped locking member 51 to stably maintain a state in which the belt-like member 15' is formed into a ring shape having a desired diameter.

FIG. 7(b) illustrates a configuration example of a pawl-type locking member 52 configured to lock the end portions of the belt-like member 15' to each other by the engagement of the pawls. In the example in FIG. 7(b), the pawl-type locking member 52 includes a casing 52a and a pawl 52c that can pivot about a shaft 52b. One end of the belt-like member 15' is fixed to the casing 52a, and the other end side of the belt-like member 15' is inserted into the casing 52a and is slidable. Sawteeth 15a are formed on the other end side of the belt-like member 15', and any one of the sawteeth 15a is locked to the pawl 52c.

The engagement relationship between the pawl 52c and the sawtooth 15a is as follows. That is, even if the pawls 52c are not caused to pivot to be retracted from the sawtooth 15a, the belt-like member 15' can be slid in a direction in which the diameter of the ring formed by the belt-like member 15' increases (the direction indicated by the right arrow in FIG. 7(b)). On the other hand, the belt-like member 15' cannot slide in a direction in which the diameter of the ring formed by the belt-like member 15' decreases (the direction indicated by the left arrow in FIG. 7(b)). In order to slide the belt-like member 15' in this direction, it is necessary to cause the pawl 52c to pivot and retract from the sawtooth 15a.

When the locking members 51 and 52 are used as illustrated in FIG. 7, the belt-like member 15' does not necessarily have a restoring force. Alternatively, the restoring force may be weak. The same applies to belt-like members 151' and 152' described with reference to FIGS. 8 and 9.

Figure 8:
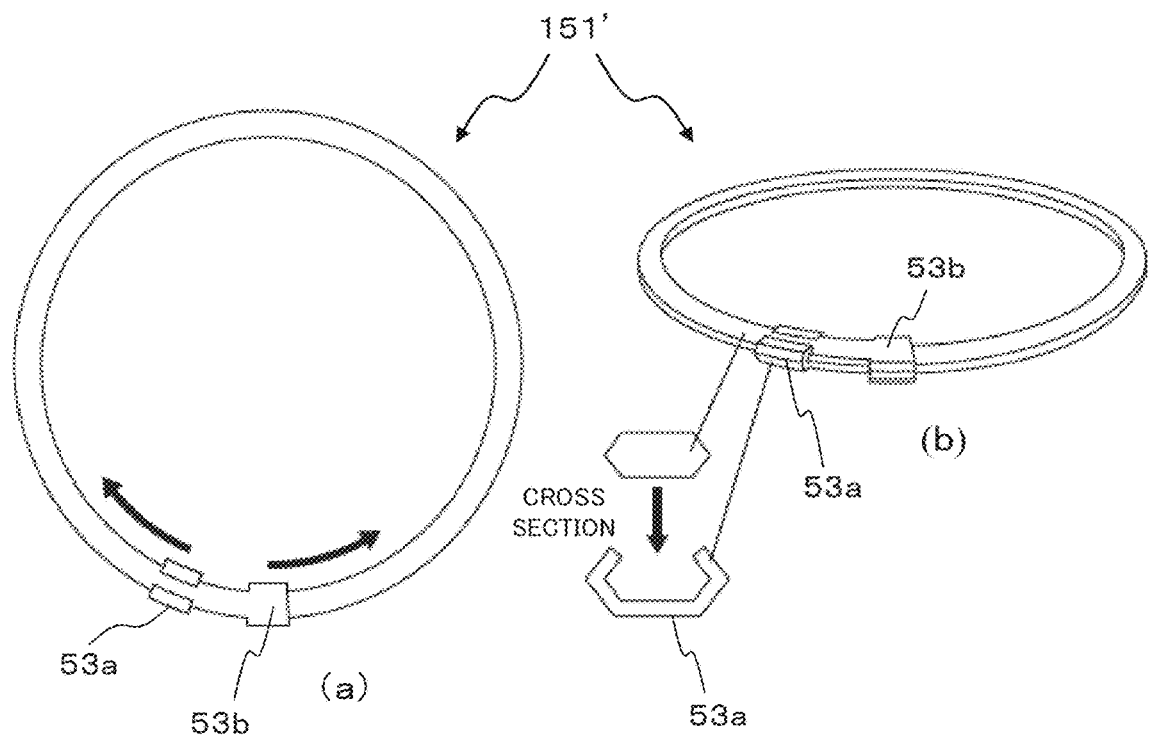
FIG. 8 is a view illustrating another example of the fixing member.

FIG. 8 is a view illustrating another configuration example of the locking member. In the example illustrated in FIG. 8, the belt-like member 151' includes locking members 53a and 53b at both ends of the belt-like member 151'. The locking members 53a and 53b are configured by fitting type locking members to which a part of the belt-like member 151' is fitted. That is, as illustrated in FIG. 8, the locking members 53a and 53b each are configured to stably grip a portion of the belt-like member 151' in accordance with the cross-sectional shape of the belt-like member 151'. The portion of the belt-like member 151' means a portion of the length of the belt-like member 151' in the longitudinal direction and a portion of the cross-sectional shape of the belt-like member 151' in the circumferential direction. The cross-sectional shape of the belt-like member 151' in the circumferential direction may configured to hold not a part but the entire circumference.

As illustrated in FIG. 8, one locking member 53a provided at one end of the belt-like member 151' grips a portion close to the other end of the belt-like member 151'. One locking member 53b provided at the other end of the belt-like member 151' grips a portion close to one end of the belt-like member 151'. The locking members 53a and 53b at both ends are formed so that the upper and lower sides are opposite to each other. One locking member 53a grips the belt-like member 151' from the lower side. The other locking member 53b grips the belt-like member 151' from the upper side. Therefore, portions of the belt-like member 151' overlap between the locking members 53a and 53b at both ends.

As described above, the locking members 53a and 53b are formed in a shape conforming to the cross-sectional shape of the belt-like member 151'. The shape conforming to the cross-sectional shape means that the cross-sectional shape of the inner portion of each of the locking members 53a and 53b is substantially the same as the cross-sectional shape of the corresponding portion of the belt-like member 151', and the sizes of the cross-sectional shapes are also substantially the same. When the locking members 53a and 53b are made of a flexible member, the cross-sectional shape of each of the inner portions of the locking members 53a and 53b may be slightly smaller than the cross-sectional shape of the corresponding portion of the belt-like member 151'. With such a configuration, it is possible to maintain a state in which the belt-like member 151' is gripped by a specific portion unless a certain external force or more is applied.

On the other hand, when the user applies an external force of the belt-like member 151', the locking members 53a and 53b can be slid along the longitudinal direction of the belt-like member 151'. This can contract or extend the belt-like member 151' by changing the portion of the belt-like member 151' in the longitudinal direction which is gripped by the locking members 53a and 53b.

In this case, contracting the belt-like member 151' means reducing the diameter of the ring shape formed by the belt-like member 151' and increasing the portion where portions of the belt-like member 151' overlap between the locking members 53a and 53b at both ends. Extending the belt-like member 151' means increasing the diameter of the ring shape formed by the belt-like member 151' and shortening the portion where portions of the belt-like member 151' overlap between the locking members 53a and 53b at both ends.

As illustrated in FIG. 8, when the locking members 53a and 53b are provided at both ends of the belt-like member 151', the belt-like member 151' does not come off from the locking members 53a and 53b only by sliding the locking members 53a and 53b. In this sense, the belt-like member 151' in FIG. 8 can also be regarded as a ring-shaped member. Accordingly, the belt-like member 151' configured as illustrated in FIG. 8 is embedded in advance in the bag-shaped portion 16 formed at the second opening peripheral edge portion of the fabric 11 and is configured integrally with the fabric 11.

Note that the locking members 53a and 53b may be formed from flexible members to allow the belt-like member 151' to be removed from the locking members 53a and 53b by manually expanding the opened portions. In this case, similarly to FIG. 6, it is also possible to insert the belt-like member 151' into the bag-shaped portion 16 having chipped portion from behind. Although the locking members 53a and 53b are provided at both ends of the belt-like member 151' in FIG. 8, a locking member may be provided at only one end. In this case, the belt-like member 151' can be removed from the locking member only by sliding the locking member provided at one end of the belt-like member 151'.

Figure 9:
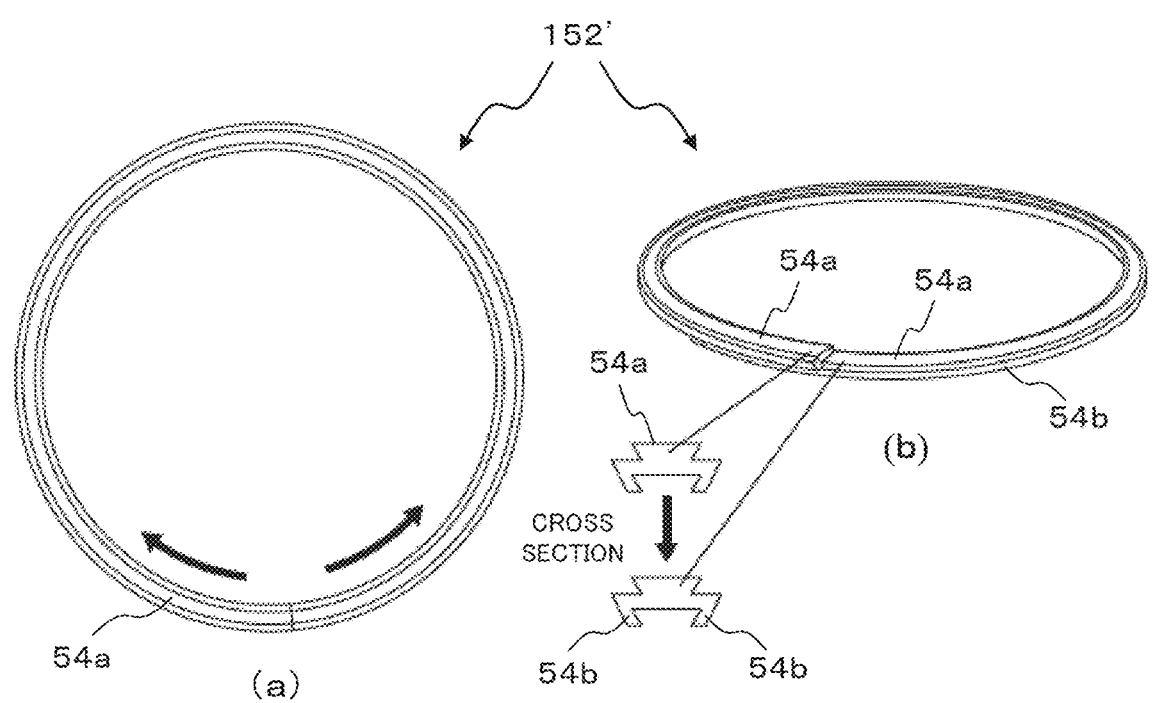
FIG. 9 is a view illustrating another example of the fixing member.

FIG. 9 is a view illustrating still another configuration example of the locking member. In the example illustrated in FIG. 9, the locking member is formed from a rail-type locking member including a rail portion 54a formed on the obverse surface of the belt-like member 152' and a leg portion 54b formed on the reverse surface of the belt-like member 152'. In the example of FIG. 9, the rail portion 54a is one rail having a trapezoidal cross-sectional shape and is formed on the entire surface of the belt-like member 152' along the longitudinal direction. The leg portion 54b is formed in a shape that sandwiches the rail portion 54a from both sides along the longitudinal direction on the entire reverse surface of the belt-like member 152' in conformity to the trapezoidal cross-sectional shape of the rail portion 54a.

In this manner, the locking member illustrated in FIG. 9 is formed such that the rail portion 54a formed on the surface on one end side of the belt-like member 152' meshes with the leg portion 54b formed on the reverse surface on the other end side of the belt-like member 152'. Accordingly, at the portion where the rail portion 54a meshes with the leg portion 54b, portions of the belt-like member 152' overlap.

As described above, the leg portion 54b is formed in a shape conforming to the cross-sectional shape of the rail portion 54a. The shape conforming to the cross-sectional shape means that the length and angle of the leg portion 54b are substantially the same as the length and angle of the side surface (portions corresponding to both legs of the trapezoid) of the rail portion 54a. When the leg portion 54b is formed from a flexible member, the angle of the leg portion 54b may be slightly smaller than the angle of the side surface of the rail portion 54a. With such a configuration, it is possible to maintain a state in which the belt-like member 152' is gripped by a specific portion unless a certain external force or more is applied.

On the other hand, when the user applies an external force to the belt-like member 152', the leg portion 54b can be slid along the longitudinal direction of the rail portion 54a. As a result, changing the length of the rail portion 54a sandwiched by the leg portion 54b in the longitudinal direction can contract or extend the belt-like member 152'.

In this case, contracting the belt-like member 152' means reducing the diameter of the ring shape formed by the belt-like member 152' and extending the portion of the belt-like member 152' where the rail portion 54a and the leg portion 54b mesh with each other. Extending the belt-like member 152' means increasing the diameter of the ring shape formed by the belt-like member 152' and shortening the portion of the belt-like member 152' where the rail portion 54a and the leg portion 54b mesh with each other.

When the locking member is configured as illustrated in FIG. 9, the leg portion 54b can be removed from the rail portion 54a only by sliding the leg portion 54b along the rail portion 54a. Therefore, the belt-like member 152' configured as illustrated in FIG. 9 may be embedded in advance in the bag-shaped portion 16 formed at the second opening peripheral edge portion of the fabric 11 or may be inserted later into the bag-shaped portion 16 having a chipped portion as in FIG. 6.

Although FIG. 9 illustrates the configuration in which the rail portion 54a is formed over the entire obverse surface of the belt-like member 152' and the leg portion 54b is formed over the entire reverse surface of the belt-like member 152', the rail portion 54 and the leg portion 54b may be formed only in the vicinity of the end portion of the belt-like member 152'.

As described above, referring to FIG. 8, the locking members 53a and 53b configured in the fitting type have shapes conforming to the cross-sectional shape of the belt-like member 151', so that the locking members 53a and 53b can stably grip a part of the belt-like member 151'. In addition, referring to FIG. 9, the rail type locking member is configured by the rail portion 54a and the leg portion 54b, and the leg portion 54b has a shape conforming to the cross-sectional shape of the rail portion 54a, so that the locking members 54a and 54b can stably grip a part of the belt-like member 152'.

In contrast to this, the belt-like member 151' may be formed as follows. That is, the cross-sectional shapes of the locking members 53a and 53b is formed to be slightly larger than the cross-sectional shape of the belt-like member 151' to make the locking members 53a and 53b easily slide along the belt-like member 151'. In addition, the belt-like member 151' is configured by a member having a restoring force to spread outward to return to the original shape (the state in which the belt-like member 151' is extended) when the application of the external force is stopped after the belt-like member 151' is deformed into a state of narrowing inward by receiving the external force (the state in which the belt-like member 151' is contracted).

In addition, the belt-like member 152' may be formed as follows. For example, the angle of the leg portion 54b is made slightly more obtuse than the angle of the rail portion 54a to make the leg portion 54b easily slide along the rail portion 54a. In addition, the belt-like member 152' is configured by a member having a restoring force to spread outward to return to the original shape (the state in which the belt-like member 152' is extended) when the application of the external force is stopped after the belt-like member 152' is deformed into a state of narrowing inward by receiving the external force (the state in which the belt-like member 152' is contracted).

When configured in this manner, the locking members 53a and 53b in FIG. 8 and the locking members 54a and 54b in FIG. 9 do not function as a locking mechanism for stably maintaining the belt-like members 151' and 152' in a constant state but function as a guide mechanism (guide member) for stably sliding the belt-like members 151' and 152' along the longitudinal direction of the belt-like members 151' and 152'.

Second Embodiment

Figure 10:
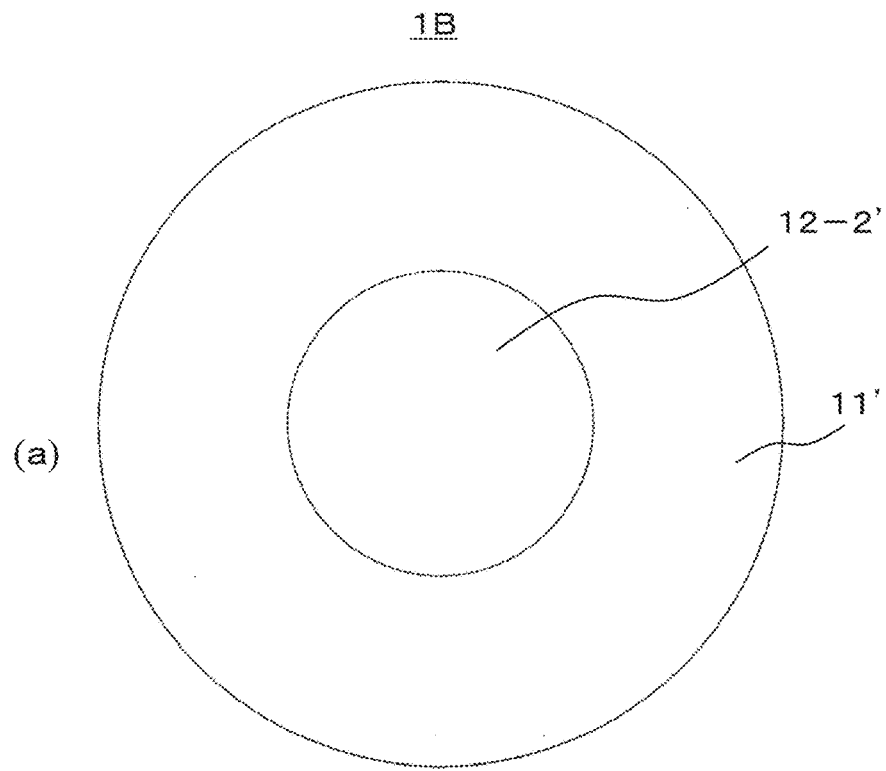
FIG. 10 is a diagram illustrating a configuration example of a headphone cover according to the second embodiment.
Figure 10:
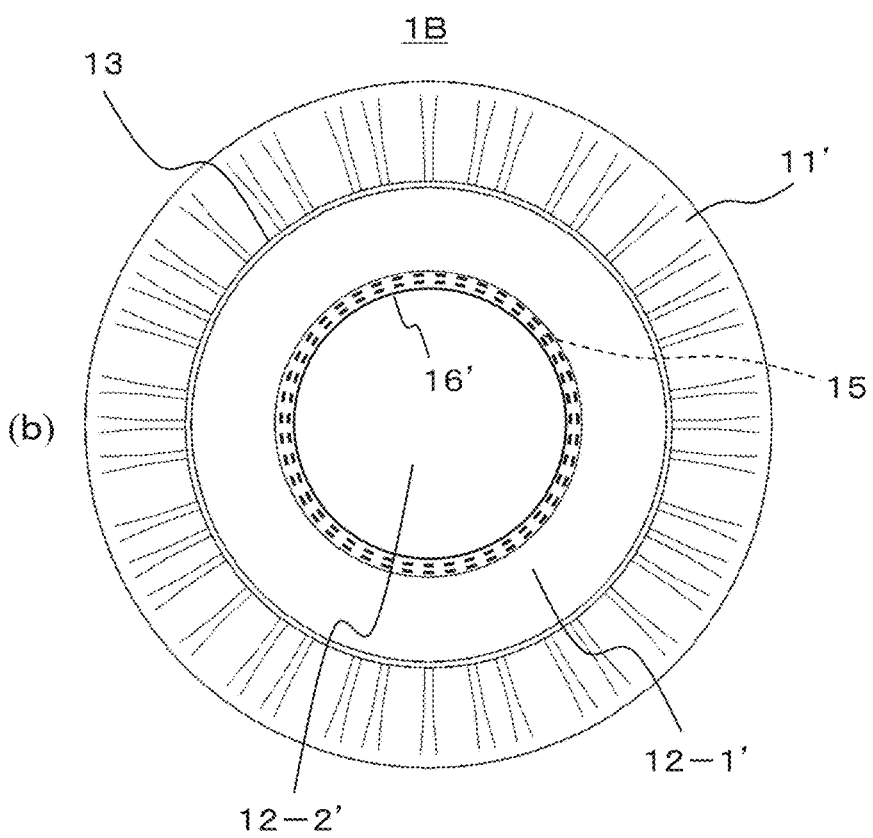

The second embodiment of the present invention will be described next with reference to the accompanying drawings. FIG. 10 is a diagram illustrating a configuration example of a headphone cover 1B according to the second embodiment, with (a) illustrating a plan view and (b) illustrating a bottom surface. The headphone cover 1B according to the present embodiment has elasticity and is deformable. FIG. 10 illustrates one aspect of the shape of the headphone cover 1B in a steady state in which no external force is applied. The headphone cover 1B according to the second embodiment is also used to cover an ear pad 101 of an around ear type headphone 100. Referring to FIG. 10, components denoted by the same reference numerals as those illustrated in FIG. 1 have the same functions, and hence redundant description will be omitted here.

In the second embodiment, a peripheral edge portion of a fabric 11' is folded back to one surface side (bottom surface side) over the entire circumference. A first opening 12-1' is formed on the one surface side, and a second opening 12-2' is formed on a non-folded surface side (flat surface side) opposite to the one surface side. Both of the two openings 12-1' and 12-2' are formed in a circular shape, and the second opening 12-2' is formed to have a smaller diameter than the first opening 12-1'.

In this case, the diameter of the first opening 12-1' is smaller than the diameter of a circle formed by the outer peripheral surface of the ear pad 101 or the outer peripheral surface of a housing 102 (in particular, a portion in contact with the ear pad 101) of the headphone 100 to be attached to the headphone cover 1B. Furthermore, the diameter of the second opening 12-2' is substantially equal to or slightly smaller or larger than the diameter of the circle formed by the inner peripheral surface of the ear pad 101. That is, the diameters of the two openings 12-1' and 12-2' are designed so as to satisfy the relationship of (diameter of circle formed by inner peripheral surface of ear pad 101)≈(diameter of second opening 12-2')<(diameter of first opening 12-1')< (diameter of circle formed by the outer peripheral surface of ear pad 101 (or housing 102)).

The first opening peripheral edge portion corresponding to the peripheral edge of the first opening 12-1' is provided with an elastic body (for example, elastic webbing) 13 for fixing the first opening peripheral edge portion to the outer peripheral surface of the ear pad 101 or the outer peripheral surface of the housing 102. Also in the second embodiment, the length of the sewing thread is set to be longer than the length of the entire circumference of the elastic webbing 13 in the most contracted state. Then, a thread is sewn substantially parallel to the longitudinal direction (circumferential direction) of the elastic webbing 13. In the second embodiment, the elastic webbing 13 is stretched, and an end portion of a fabric 11' that is not stretched and the elastic webbing 13 are stitched together. The same applies to the third embodiment described later.

In addition, size setting is performed such that the length of the circumference of the elastic webbing 13 in the non-stretched state is longer than the length of the circumference of the end portion of the fabric 11' in the non-stretched state. As a result, after the elastic webbing 13 is sewn to the fabric 11' in a stretched state, when the stretched state is returned to a steady state by stopping the stretching, the first opening peripheral edge portion is contracted by the force of the elastic webbing 13 to generate a wrinkle. That is, the end portion of the fabric 11' is sewn to the elastic webbing 13 in a state in which the first opening peripheral edge portion is loosened. The same applies to the third embodiment described later.

At the second opening peripheral edge portion corresponding to the peripheral edge of the second opening 12-2, a fixing member for fixing a part of the fabric 11 to the inner peripheral surface of the ear pad 101 or its vicinity when the headphone cover 1B is attached to the headphone 100 is provided. In the present embodiment, the part of the fabric 11' is the second opening peripheral edge portion of the second opening 12-2'.

As a fixing member, a member similar to that in the first embodiment can be used. For example, the ring-shaped member 15 illustrated in FIG. 1 can be used as a fixing member. The ring-shaped member 15 is embedded in a bag-shaped portion 16' formed at the second opening peripheral edge portion of the second opening 12-2'. The bag-shaped portion 16' is formed by folding back the second opening peripheral edge portion of the fabric 11 over the entire circumference and sewing the side close to the distal end of the folded portion with a yarn.

Figure 6:
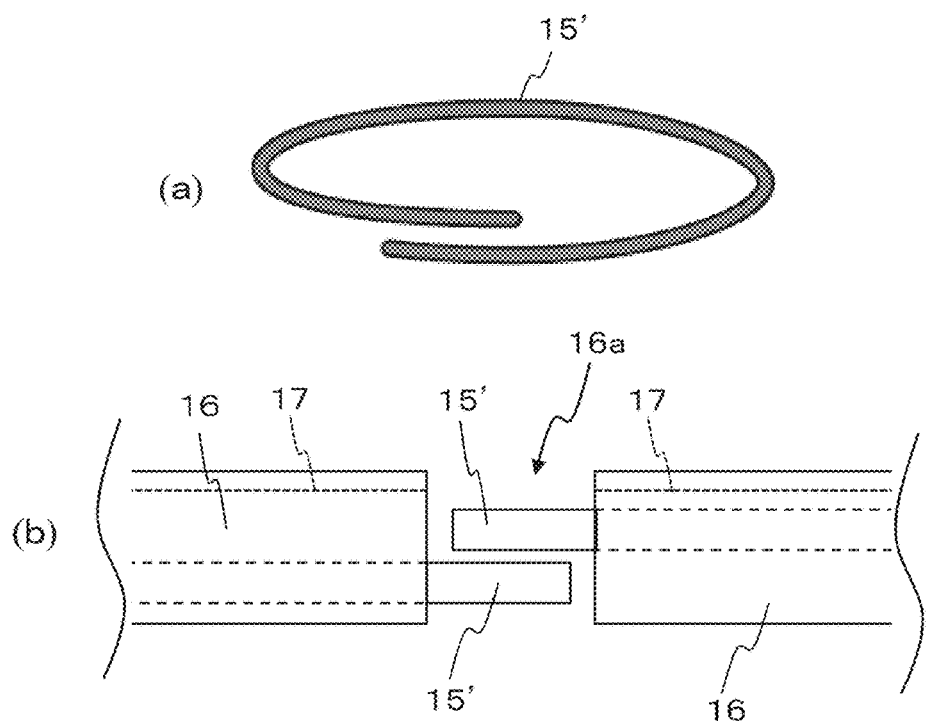
FIG. 6 is a view illustrating another example of the fixing member.
Figure 7:
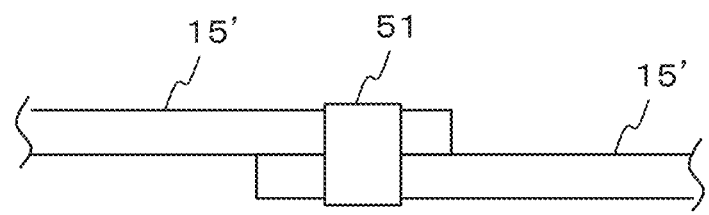
FIG. 7 is a view illustrating a configuration example of a locking member that locks the ends of a belt-like member to each other.
Figure 7:
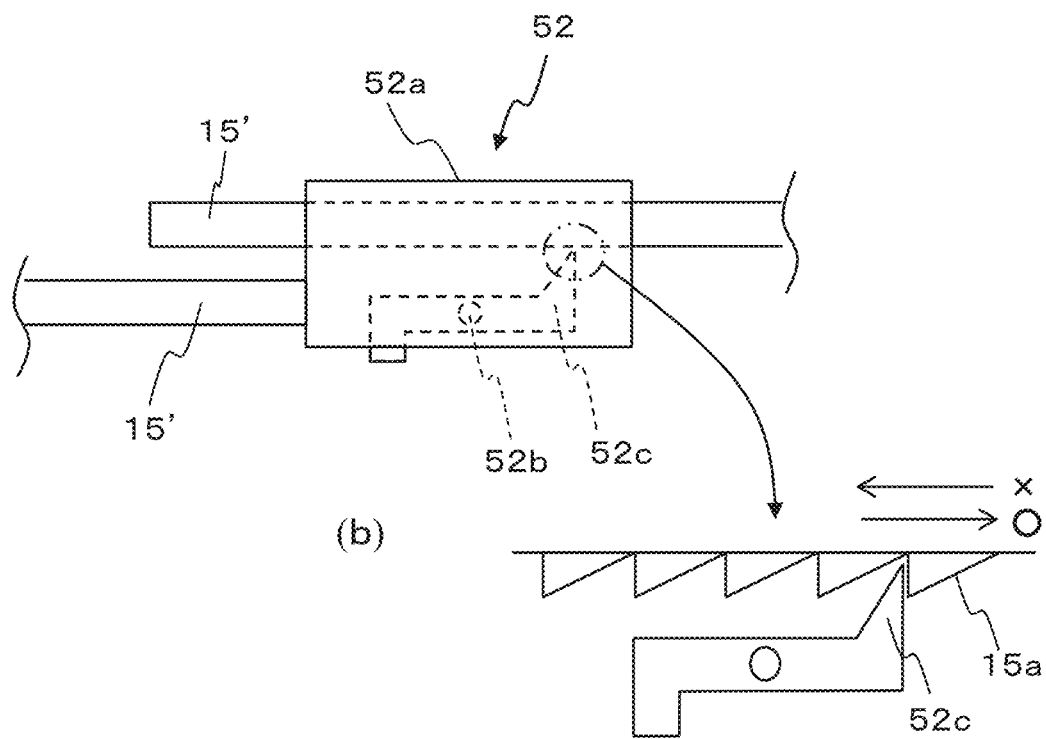

Instead of the ring-shaped member 15, the ring-shaped member 151 illustrated in FIG. 4, the ring-shaped member 152 illustrated in FIG. 5, or the belt-like member 15' illustrated in FIG. 6 may be used. When the belt-like member 15' is used, the locking members 51 and 52 as illustrated in FIG. 7 may be further used. Further, instead of the ring-shaped member 15, the belt-like member 151' illustrated in FIG. 8 or the belt-like member 152' illustrated in FIG. 9 may be used.

With a configuration like that according to the second embodiment, even when the ear pad 101 is covered with the fabric 11 of the headphone cover 1B (similar to the state in FIG. 2), the cylindrical recessed space 105 formed in the middle portion of the ear pad 101 can be prevented from being blocked by the fabric 11 of the headphone cover 1B. This enables the user to use an around ear type headphone 100 attached with the headphone cover 1B according to the present embodiment with a sense of use similar to that of an around ear type.

Figure 11:
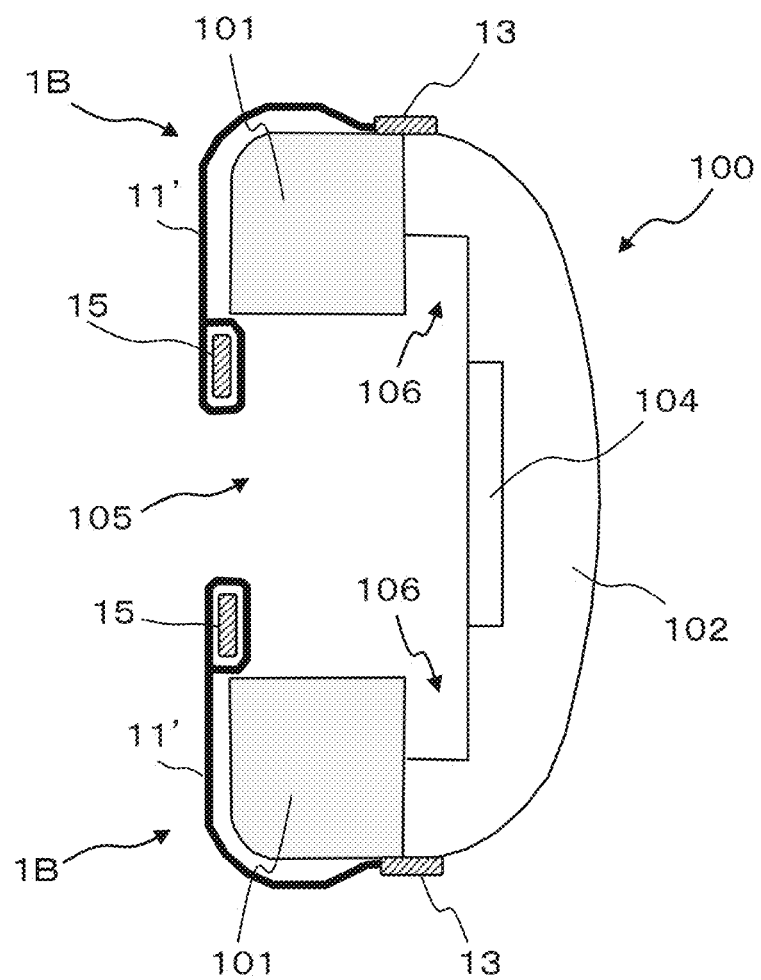
FIG. 11 is a schematic diagram illustrating a state in which the headphone covers according to the second embodiment are attached to the headphone.

Furthermore, according to the second embodiment, as illustrated in FIG. 11, while the first opening peripheral edge portion of the fabric 11' is fixed to the outer peripheral surface of the ear pad 101 or the housing 102 by the elastic webbing 13, the headphone cover 1B can be used without placing the second opening peripheral edge portion (fixing member) of the fabric 11' in the gap 106 between the reverse surface of the ear pad 101 and the housing 102. In this case, a part of the ear comes into contact with the fabric 11', but since the portion of the second opening 12-2' is released, there is no oppressive feeling as in a perfect on-ear type headphone, and direct sound that does not pass through the fabric 11' can be heard from the loudspeaker unit 104.

Third Embodiment

Figure 12:
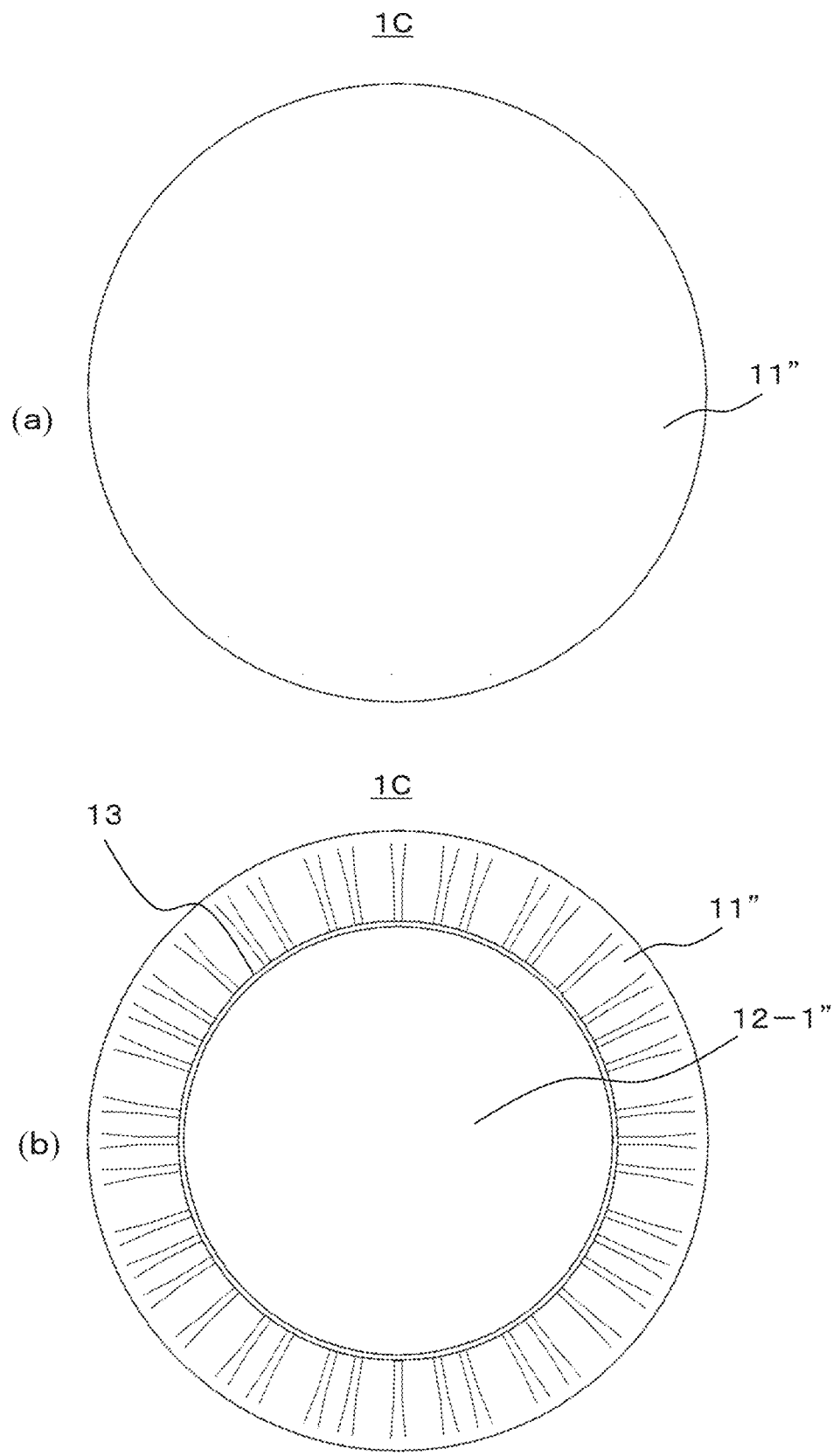
FIG. 12 is a diagram illustrating a configuration example of a headphone cover according to the third embodiment.

The third embodiment of the present invention will be described next with reference to the accompanying drawings. FIG. 12 is a diagram illustrating a configuration example of a headphone cover 1C according to the third embodiment, with (a) illustrating a plan view and (b) illustrating a bottom surface. The headphone cover 1C according to the present embodiment has elasticity and is deformable. FIG. 12 illustrates one aspect of the shape of the headphone cover 1C in a steady state in which no external force is applied. The headphone cover 1C according to the third embodiment is also used to cover an ear pad 101 of an around ear type headphone 100. Referring to FIG. 12, components denoted by the same reference numerals as those illustrated in FIG. 10 have the same functions, and hence redundant description will be omitted here.

In the third embodiment, the peripheral edge portion of a fabric 11" is folded back to one surface side (bottom surface side) over the entire circumference, and an opening 12-1" is formed on the one surface side. This opening 12-1" is similar to the first opening 12-1' in the second embodiment. In the third embodiment, the second opening 12-2' in the second embodiment is not present.

The opening peripheral edge portion corresponding to the peripheral edge of the opening 12-1" is provided with an elastic body (for example, elastic webbing) 13 for fixing the opening peripheral edge portion to the outer peripheral surface of the ear pad 101 or the outer peripheral surface of the housing 102. This point is similar to that in the second embodiment.

In the third embodiment, the fixing member is not integrally formed with the fabric 11". That is, the fixing member is not embedded in the bag-shaped portion of the fabric 11" to be integrated. For example, in the third embodiment, it is preferable to use a belt-like member 15' as a fixing member and to use a locking member 51 or 52 as illustrated in FIG. 7. It is also preferable to use the belt-like member 151' (a member having the locking members 53a and 53b functioning as a locking mechanism) illustrated in FIG. 8 or the belt-like member 152' (a member having the locking members 54a and 54b functioning as a locking mechanism) illustrated in FIG. 9 as a fixing member.

Alternatively, the ring-shaped member 15 illustrated in FIG. 1, the ring-shaped member 151 illustrated in FIG. 4, the ring-shaped member 152 illustrated in FIG. 5, the belt-like member 151' (a member having the locking members 53a and 53b functioning as a guide mechanism) illustrated in FIG. 8, or the belt-like member 152' (a member having the locking members 54a and 54b functioning as a guide mechanism) illustrated in FIG. 9 may be used as a fixing member having a diameter that allows insertion into the gap 106 between the ear pad 101 and the housing 102 and having a restoring force to try to return to the original ring shape when no external force is applied.

In the third embodiment, the fixing member fixes a part of the fabric 11" on the unfolded surface side (flat surface side) opposite to the one surface side (bottom surface side) of the fabric 11" to the inner peripheral surface of the ear pad 101 or its vicinity (the gap 106). The portion of the fabric 11" refers to a portion around the position where the opening peripheral edge portion of the second opening 12-2' in the second embodiment exists.

Figure 13:
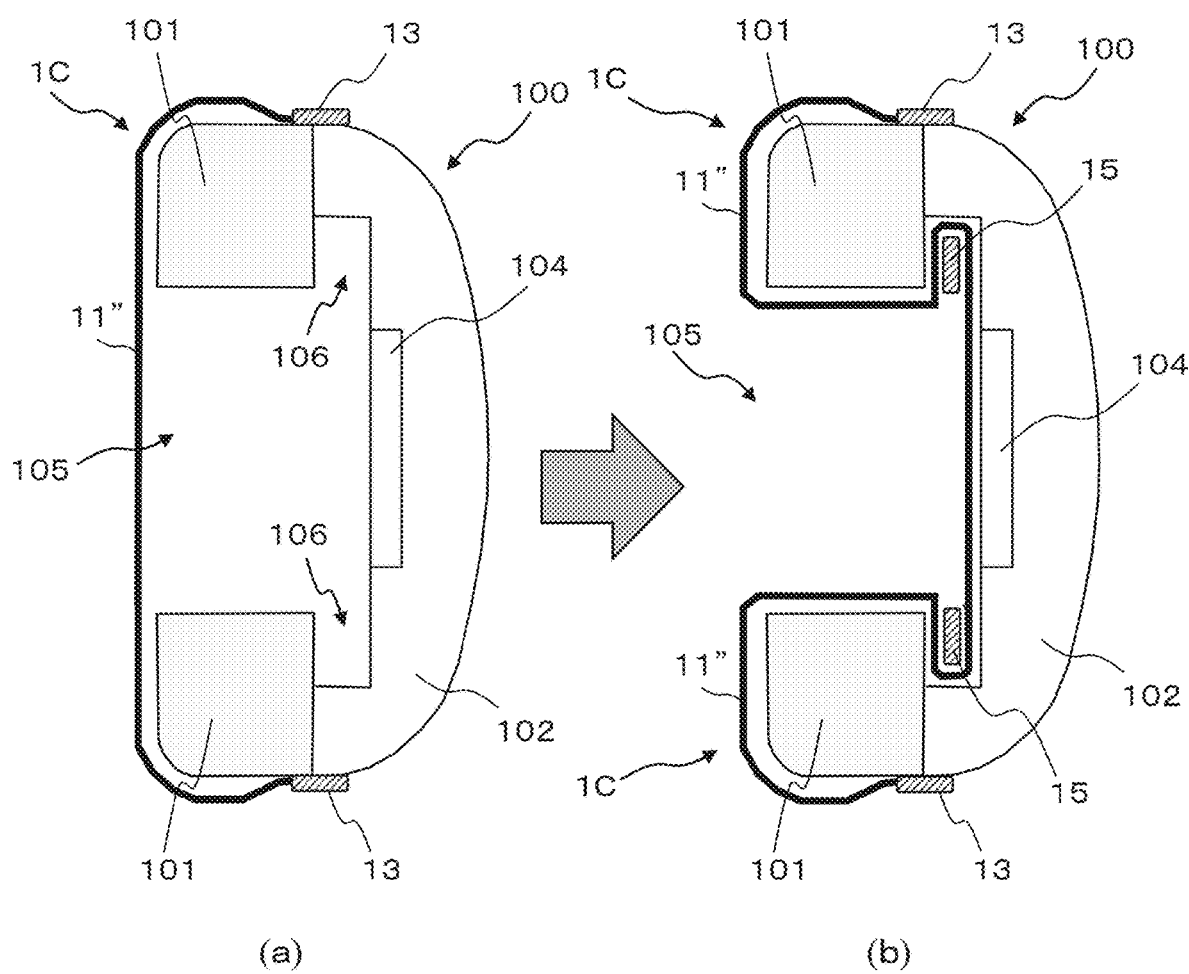
FIG. 13 is a schematic diagram illustrating a state in which the headphone covers according to the third embodiment are attached to the headphone.

FIG. 13 is a schematic diagram illustrating a state in which the headphone covers 1C according to the third embodiment are attached to the headphone 100. When the headphone cover 1C is to be attached to the headphone 100, first of all, as illustrated in FIG. 13(a), the opening 12-1 "of the fabric 11" is expanded so that the entire ear pad 101 is covered with the fabric 11", and the elastic webbing 13 sewn to the opening peripheral edge portion of the fabric 11" is hooked on the outer peripheral surface of the ear pad 101 or the housing 102, so that the opening peripheral edge portion is fixed to the outer peripheral surface of the ear pad 101 or the housing 102. At this stage, the fabric 11" closes the cylindrical recessed space 105.

Next, as illustrated in FIG. 13(b), the fixing member is pressed into the gap 106 between the ear pad 101 and the housing 102 together with a part of the fabric 11" by pressing the fixing member against the fabric 11" from above while extending the fabric 11" that closes the cylindrical recessed space 105 and pushing down the fabric 11" toward the bottom of the ear pad 101. Thus, the ear pad 101 is covered with the fabric 11" in a state in which a part of the fabric 11" is fixed in the gap 106.

In this way, even when the ear pad 101 is covered with the fabric 11" of the headphone cover 1C, the cylindrical recessed space 105 formed in the middle portion of the ear pad 101 can be prevented from being blocked by the fabric 11" of the headphone cover 1C. This enables the user to use an around ear type headphone 100 attached with the headphone cover 1C according to the present embodiment with a sense of use similar to that of an around ear type.

Furthermore, according to the third embodiment, as illustrated in FIG. 13(a), while the opening peripheral edge portion of the fabric 11" is fixed to the outer peripheral surface of the ear pad 101 or the housing 102 by the elastic webbing 13, the headphone cover 1C can be used without placing a part of the fabric 11" in the gap 106 between the ear pad 101 and the housing 102. In this case, it is possible to obtain a sense of use similar to that of an on-ear type headphone. The user can use the headphone cover 1C in either the state in FIG. 13(a) or the state in FIG. 13(b) according to the preference at that time.

In the third embodiment, an example in which the fixing member is not integrally formed with the fabric 11" has been described, but the present invention is not limited to this. For example, a bag-shaped portion may be formed at a position corresponding to a position where the opening peripheral edge portion of the second opening 12-2' in the second embodiment exists, and a fixing member may be embedded in the bag-shaped portion, so that the fixing member is integrally formed with the fabric 11".

Figure 14:
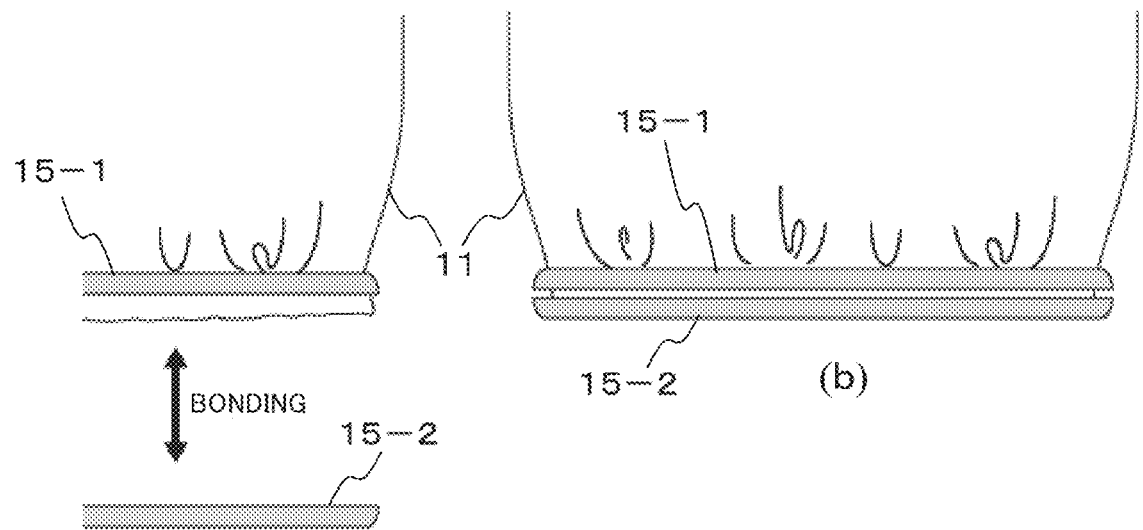
FIG. 14 is a view illustrating another example of the fixing member.
Figure 14:
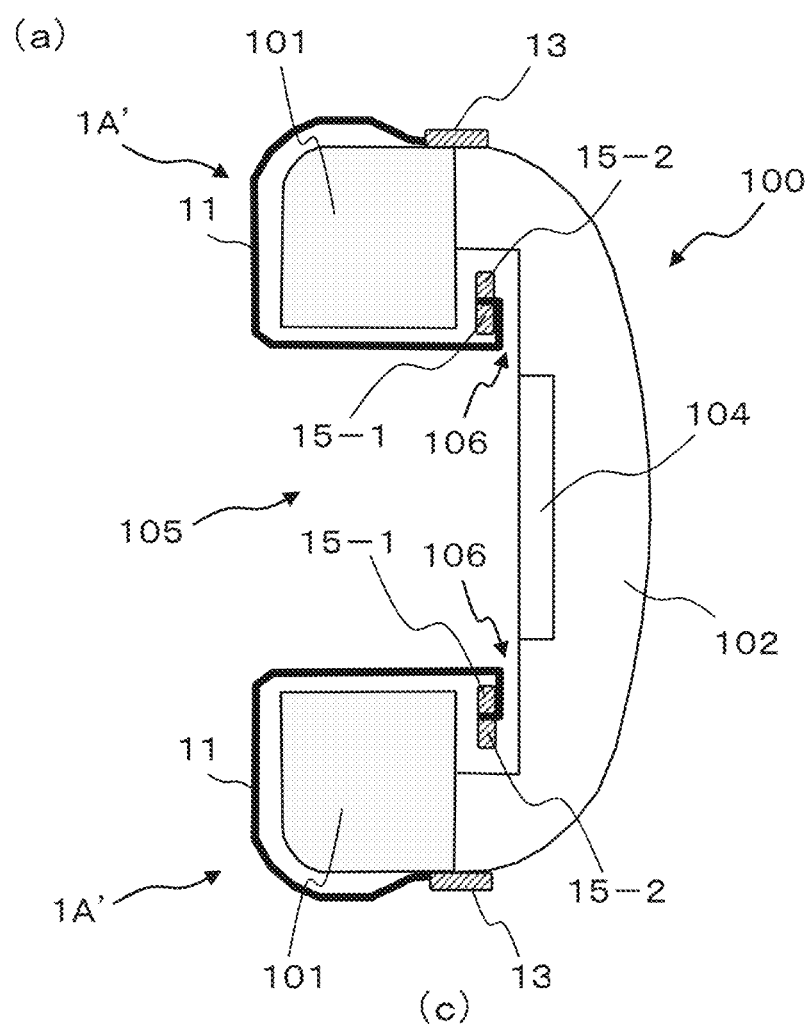
Figure 15:
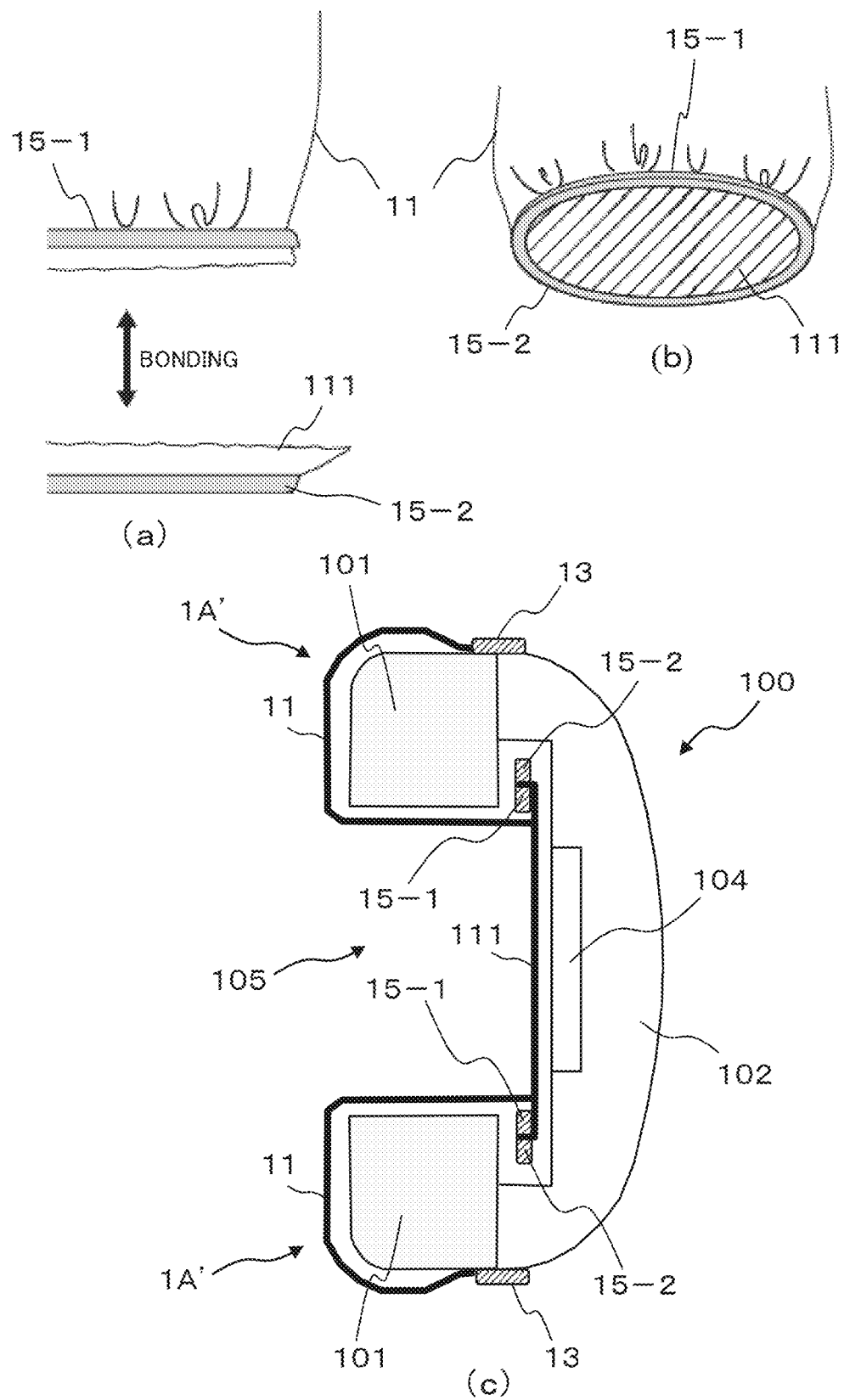
FIG. 15 is a view illustrating another example of the fixing member.

The first and second embodiments have exemplified the configuration in which the fixing member is embedded in the bag-shaped portions 16 and 16' formed at the second opening peripheral edge portions of the fabrics 11 and 11', but the present invention is not limited to this. For example, by bonding fixing members separate from the fabrics 11 and 11' to the second opening peripheral edge portions of the fabrics 11 and 11', the fixing members may be configured integrally with the fabrics 11 and 11'. Bonding can be performed using, for example, an adhesive, a hook-and-loop fastener, or the like. FIGS. 14 and 15 are diagrams illustrating a configuration example in which fixing members are bonded to the second opening peripheral edge portions of the fabrics 11 and 11'. FIGS. 14 and 15 illustrate an example in which a fixing member is bonded to the tubular fabric 11 illustrated in the first embodiment.

For example, as illustrated in FIG. 14(a), in the vicinity of the second opening peripheral edge portion of the fabric 11, a first ring-shaped member 15-1 is bonded to a portion located inwardly from the distal end of the fabric 11 by a predetermined length. Further, as illustrated in FIG. 14(b), a second ring-shaped member 15-2 is bonded to the fabric 11 such that a portion of the fabric 11 which protrudes from the bonded first ring-shaped member 15-1 to the distal end side is sandwiched between the first ring-shaped member 15-1 and the second ring-shaped member 15-2, and the second ring-shaped member 15-2 is brought into close contact with the first ring-shaped member 15-1. At this time, when an end portion of the fabric 11 protrudes from between the two ring-shaped members 15-1 and 15-2, an end treatment such as cutting the protruding portion is performed.

FIG. 14(c) is a diagram illustrating a state in which a headphone cover 1A' formed by bonding the ring-shaped members 15-1 and 15-2 from the outside of the fabric 11 as illustrated in FIG. 14(b) is attached to the headphone 100. This state is the same as the state illustrated in FIG. 2 except that the ring-shaped members 15-1 and 15-2 are not covered with the fabric 11. In this case, the two ring-shaped members 15-1 and 15-2 are bonded to the fabric 11 in order to improve the appearance. Instead of this configuration, only the first ring-shaped member 15-1 may be used.

FIG. 15 illustrates a configuration example in which a fabric 111 is provided inside the second ring-shaped member 15-2. FIG. 15 is the same as FIG. 14 except for the fabric 111. Referring to FIG. 15, in the vicinity of the peripheral edge of the fabric 111, the second ring-shaped member 15-2 is bonded to a portion of the fabric 111 which is located inwardly from the distal end by a predetermined length. Further, an end portion of the fabric 11 is bonded to an end portion of the fabric 111 such that a portion of the fabric 11 which protrudes from the first ring-shaped member 15-1 to the distal end side and a portion of the fabric 111 which protrudes from the second ring-shaped member 15-2 to the distal end side are sandwiched between the two ring-shaped members 15-1 and 15-2, and the second ring-shaped member 15-2 is brought into close contact with the first ring-shaped member 15-1. At this time, when end portions of the fabrics 11 and 111 protrude from between the two ring-shaped members 15-1 and 15-2, an end treatment such as cutting the protruding portions is performed.

Figure 16:
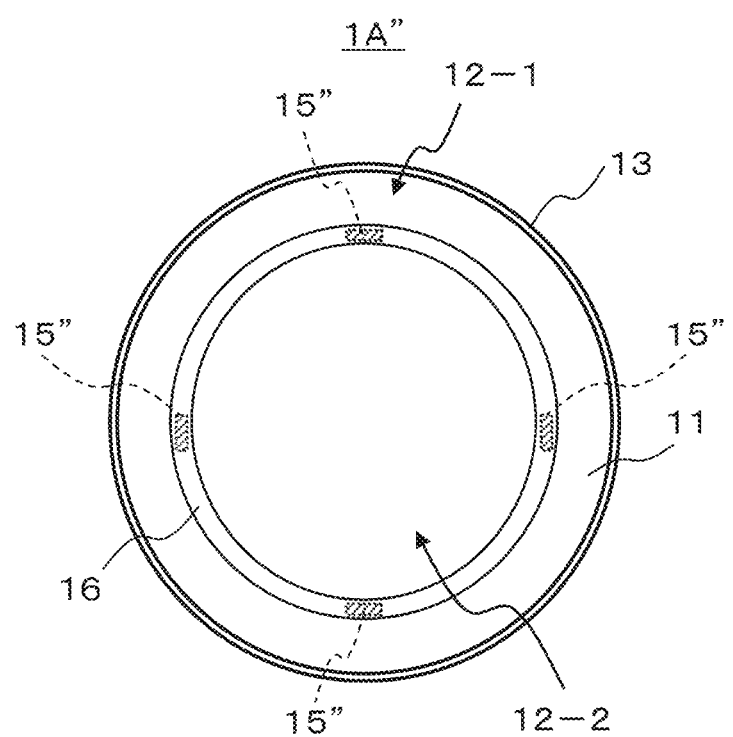
FIG. 16 is a view illustrating another example of the fixing member.

The first to third embodiments have exemplified the cases in which the ring-shaped members 15, 151, and 152 or the ring-shaped belt-like members 15', 151', and 152' are used as fixing members, but the present invention is not limited to them. For example, as illustrated in FIG. 16, a fixing member may be configured by a plurality of block-shaped members 15" that are neither ring-shaped nor belt-like. In the example in FIG. 16, four block-shaped members 15" are used instead of the ring-shaped members 15 and 15' described in the first embodiment, and a part of the fabric 11 is fixed to the inner peripheral surface of the ear pad 101 or its vicinity by the four block-shaped members 15".

In the case of using the block-shaped member 15", since it is not possible to fix the fabric 11 by using the restoring force to return to the original shape like the ring-shaped member 15, 151, and 152 and the belt-like members 15', 151', and 152' or to fix the fabric 11 by maintaining the size of the ring shape using the locking member, the block-shaped member 15" is embedded in the gap 106 to fix the fabric 11. Similarly, a part of the fabric 11' described in the second embodiment or a part of the fabric 11" described in the third embodiment can be fixed by a plurality of block-shaped members 15" in the gap 106.

In addition, the first to third embodiments have exemplified the cases in which the shapes of the fabrics 11, 11', and 11" are circular, but the present invention is not limited to them. For example, the shape of each of the fabrics 11, 11', and 11" may be an elliptical shape, a triangular shape, a quadrangular shape, or a polygonal shape of pentagon or more. In addition, the above embodiments have exemplified the cases in which the shapes of the openings 12-1, 12-2, 12-1', 12-2', and 12-1" are circular, but the present invention is not limited to them. For example, the shape of each of the openings 12-1, 12-2, 12-1', 12-2', and 12-1" may be an elliptical shape, a triangular shape, a quadrangular shape, or a polygonal shape of pentagon or more.

The first and second embodiments have exemplified the configuration in which the fixing member is embedded in the bag-shaped portions 16 and 16' formed at the fabrics 11 and 11', but the present invention is not limited to this. For example, as in the third embodiment, the bag-shaped portions 16 and 16' may not be provided, and the fixing member and the fabrics 11 and 11' may be configured so as not to be integrated.

In addition, the first to third embodiments are merely examples of embodying the present invention, and the technical scope of the present invention should not be interpreted in a limited manner by these embodiments. That is, the present invention can be implemented in various forms without departing from the gist or main features of the present invention.

REFERENCE SIGNS LIST 1A, 1B, 1C headphone cover
11, 11', 11" fabric
12-1, 12-2, 12-1', 12-2', 12-1" opening
13 elastic webbing (elastic body)
15, 151, 152 ring-shaped member (fixing member)
15', 151', 152' belt-like member (fixing member)
15" block-shaped member (fixing member)
16 bag-shaped portion
51, 52, 53a, 53b locking member
54a rail portion (locking member)
54b leg portion (locking member)

The invention claimed is:

1. A headphone cover used covering an ear pad of an around ear type headphone, characterized by comprising:
   a fabric configured to cover the ear pad from an outer peripheral surface of the ear pad to an inner peripheral surface of the ear pad; and
   a fixing member formed as a separate body from the fabric and configured to fix a part of the fabric to the inner peripheral surface of the ear pad or a vicinity of the inner peripheral surface by acting in a direction from a recessed space formed inside the ear pad to the inner peripheral surface of the ear pad,
   wherein
   the fixing member includes a ring-shaped member or a belt-like member formed in a ring shape configured to be deformable between a state of narrowing inward and a state of spreading outward;
   the fixing member is configured to spread outward to be able to maintain a deformed state until a part of the fabric is guided to an inner peripheral surface of the ear pad or a vicinity of the inner peripheral surface; and
   an opening peripheral edge portion corresponding to a peripheral edge of an opening formed at a predetermined position on the fabric is configured to be fixable to an outer peripheral surface of the ear pad or an outer peripheral surface of a housing, and a part of the fabric is configured to be fixable to an inner peripheral surface of the ear pad or a vicinity of the inner peripheral surface by the fixing member.

2. The headphone cover according to claim 1, characterized in that the fixing member is configured to have a ring shape as a whole by sequentially coupling a plurality of plates, and
   each of the plurality of plates is connected to another plate through a rotation shaft provided near both ends and is configured to be pivotal about the rotation shaft.

3. The headphone cover according to claim 1, characterized in that the fixing member includes a flexible member having flexibility and a spring member disposed between both ends of the flexible member and is a ring-shaped member being configured to have a ring shape as a whole by the flexible member and the spring member,
   wherein the fixing member has a restoring force to spread outward to return to an original shape when application of an external force is stopped after the fixing member is deformed to a state of narrowing inward by application of an external force so that is configured to be deformable between a state of narrowing inward and a state of spreading outward.

4. The headphone cover according to claim 1, characterized in that the fixing member is a belt-like member configured to be deformable between a state of narrowing inward in the ring shape and a state of spreading outward and has a restoring force to spread outward to return to an original shape when application of an external force is stopped after the fixing member is deformed to a state of narrowing inward by application of an external force, and further comprising a guide member configured to guide the belt-like member formed in the ring shape to stably slide along a longitudinal direction of the belt-like member.

5. The headphone cover according to claim 1, characterized in that the fixing member is a belt-like member configured to be deformable between a state of narrowing inward in the ring shape and a state of spreading outward, and includes a locking member configured to lock at least a part of the belt-like member so as to maintain a state in which the belt-like member is deformed and formed in a ring shape,
wherein
the locking member is formed from a pawl-type locking member including a casing and a pawl that is pivotal about a shaft, and
one end of the belt-like member is fixed to the casing, the other end side of the belt-like member is slidable inside the casing, and any one of sawtooth formed on the other end side of the belt-like member is locked to the pawl.

6. The headphone cover according to claim 1, characterized in that the fixing member is a belt-like member configured to be deformable between a state of narrowing inward in the ring shape and a state of spreading outward, and includes a locking member configured to lock at least a part of the belt-like member so as to maintain a state in which the belt-like member is deformed and formed in a ring shape,
wherein
the locking member is formed from a rail-type locking member including a rail portion formed on an obverse surface of the belt-like member and a leg portion formed on a reverse surface of the belt-like member, and
the rail portion formed on an obverse surface on one end side of the belt-like member and the leg portion formed on a reverse surface on the other end side of the belt-like member are formed to mesh with each other.

7. A fastener for holding a headphone cover on an ear pad of an around ear type headphone, characterized by comprising a fixing member configured to act in a direction from a recessed space formed inside the ear pad to an inner peripheral surface of the ear pad to fix a part of a fabric to the inner peripheral surface of the ear pad or a vicinity of the inner peripheral surface,
wherein
the fixing member includes a ring-shaped member or a belt-like member formed in a ring shape configured to be deformable between a state of narrowing inward and a state of spreading outward;
the fixing member is configured to spread outward to be able to maintain a deformed state until a part of the fabric is guided to an inner peripheral surface of the ear pad or a vicinity of the inner peripheral surface; and
the fixing member being sized to fit in a gap existing between a reverse surface of the ear pad of the headphone and a housing.

8. The fastener according to claim 7, characterized in that the fixing member is configured to have a ring shape as a whole by sequentially coupling a plurality of plates, and
each of the plurality of plates is connected to another plate through a rotation shaft provided near both ends and is configured to be pivotal about the rotation shaft.

9. The fastener according to claim 7, characterized in that the fixing member is a belt-like member configured to be deformable between a state of narrowing inward in the ring shape and a state of spreading outward and has a restoring force to spread outward to return to an original shape when application of an external force is stopped after the fixing member is deformed to the state of narrowing inward by application of an external force, and
further comprising a guide member configured to guide the belt-like member formed in the ring shape to stably slide along a longitudinal direction of the belt-like member.

10. The fastener according to claim 7, characterized in that the fixing member is a belt-like member configured to be deformable between a state of narrowing inward in the ring shape and a state of spreading outward, and includes a locking member configured to lock at least a part of the belt-like member so as to maintain a state in which the belt-like member is deformed and formed in a ring shape,
wherein
the locking member is formed from a pawl-type locking member including a casing and a pawl that is pivotal about a shaft, and
one end of the belt-like member is fixed to the casing, the other end side of the belt-like member is slidable inside the casing, and any one of sawtooth formed on the other end side of the belt-like member is locked to the pawl.

11. The fastener according to claim 7, characterized in that the fixing member includes a flexible member having flexibility and a spring member disposed between both ends of the flexible member and is a ring-shaped member being configured to have a ring shape as a whole by the flexible member and the spring member,
wherein the fixing member has a restoring force to spread outward to return to an original shape when application of an external force is stopped after the fixing member is deformed to a state of narrowing inward by application of an external force so that is configured to be deformable between a state of narrowing inward and a state of spreading outward.

12. The fastener according to claim 7, characterized in that the fixing member is a belt-like member configured to be deformable between a state of narrowing inward in the ring shape and a state of spreading outward, and includes a locking member configured to lock at least a part of the belt-like member so as to maintain a state in which the belt-like member is deformed and formed in a ring shape,
wherein the locking member is formed from a rail-type locking member including a rail portion formed on an obverse surface of the belt-like member and a leg portion formed on a reverse surface of the belt-like member, and
the rail portion formed on an obverse surface on one end side of the belt-like member and the leg portion formed on a reverse surface on the other end side of the belt-like member are formed to mesh with each other.

* * * * *